United States Patent [19]

Mak et al.

[11] Patent Number: 5,700,682
[45] Date of Patent: Dec. 23, 1997

[54] MECHANISM BASED SCREEN FOR RETINOID X RECEPTOR AGONISTS AND ANTAGONISTS

[75] Inventors: Paul Mak, East Windsor, N.J.; Sotirios K. Karathanasis, Rockland, N.Y.

[73] Assignee: American Cyanamid Company, Madison, N.J.

[21] Appl. No.: 465,783

[22] Filed: Jun. 6, 1995

Related U.S. Application Data

[63] Continuation of Ser. No. 999,071, Dec. 31, 1992.
[51] Int. Cl.$^6$ .................................................. C12N 1/21
[52] U.S. Cl. .................. 435/252.3; 435/7.1; 435/7.2; 435/69.1; 435/252.33; 435/325; 435/254.2; 530/300; 530/350; 536/23.1; 536/23.5
[58] Field of Search ..................... 435/7.1, 7.2, 69.1, 435/252.3, 252.33, 240.1, 320.1, 254.2; 530/300, 350; 536/23.1, 23.5

[56] References Cited

FOREIGN PATENT DOCUMENTS

| | | |
|---|---|---|
| 0441483 | 8/1991 | European Pat. Off. . |
| 0441883 | 8/1991 | European Pat. Off. . |
| WO93/25223 | 12/1993 | WIPO . |

OTHER PUBLICATIONS

Rottman et al., Molecular and Cellular Biology, 11:3814–3820 (1991).

Windom et al., Molecular and Cellular Biology, 12:3380–3389 (1992).

Karathansis: "Apolipoprotein Al gene regulation by members of the steroid/thyroid hormone . . . ", pp. 21–32 of *High density lipoproteins and atherosclerosis III*, (Miller et al. eds. 1992).

Ladias et al. (1991) Science 251:561–565.

Mak et al. (1989) J. Biol. Chem. 214:21613–21618.

McDonnell et al. (1991) J. Ster. Bioch. Mol. Biol. 39:291–297.

Yu et al. (1991) Cell 67:1251–1266.

*Primary Examiner*—Stephen Walsh
*Assistant Examiner*—Kenneth A. Sorensen
*Attorney, Agent, or Firm*—Elizabeth M. Barnhard

[57] ABSTRACT

A method is described for screening retinoid X receptor agonists or antagonists using a retinoid X receptor expressed by a yeast expression system to screen a compound having a retinoid X receptor agonist or antagonist activity. Another screen is described for detecting a compound having retinoid X receptor agonist or antagonist activity by: (1) providing a yeast strain which expresses the retinoic acid receptor and activates a reporter plasmid containing apolipoprotein AI gene site A or a mutated variant thereof; (2) incubating the compound in suitable media and a colorless chromogenic substrate; and (3) examining the media for development of color. Mutated variants of apolipoprotein AI gene site A which respond selectively to the retinoid X receptor or respond to receptors other than RXRα are also described.

11 Claims, 9 Drawing Sheets

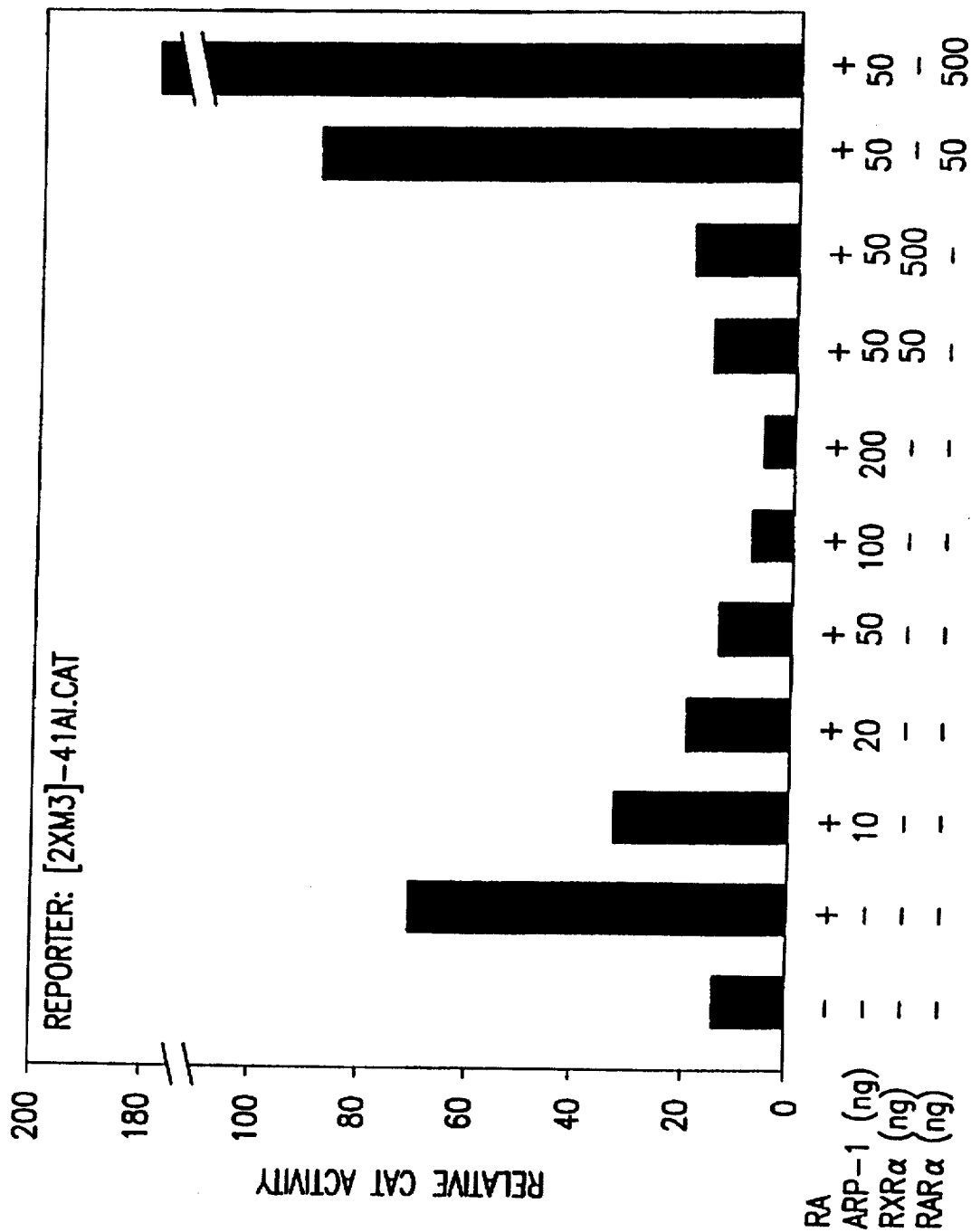

MECHANISM BASED SCREEN FOR RETINOID X RECEPTOR AGONISTS AND ANTAGONISTS

This is a continuation of copending application Ser. No. 07/999,071 filed on Dec. 31, 1992.

BACKGROUND OF THE INVENTION

1. Field of the Invention

The present invention relates to a novel screening method for the retinoid X receptor using a yeast-based expression system. The use of this yeast system enhances the ability to screen for agonists and/or antagonists of the steroid/thyroid receptor superfamily.

2. Description of the Related Art

Increased concentrations of high density lipoproteins (HDL) in the plasma are associated with protection against coronary artery disease manifested by atherosclerosis. The major protein constituent of HDL is apolipoprotein AI (apoAI), a lipid binding protein involved in the transport of cholesterol and other lipids in the plasma. Mutations that inactivate the gene coding for apoAI cause deficiencies in apoAI and HDL plasma levels associated with severe premature atherosclerosis.

Retinoic acids or vitamin A derivatives are essential for diverse aspects of development and differentiation. Recent cloning of the retinoid X receptor (RXRα) revealed that this protein is a novel member of the steroid/thyroid receptor superfamily of ligand dependent transcription factors. One of the potent targets for RXRα action is the gene encoding for apoAI. In mammals, the apoAI gene is expressed predominantly in the liver and the intestine. Recent evidence suggests that increased transcription rates of the gene coding for apoAI are associated with increased liver apoAI mRNA steady state levels and increased plasma apoAI and HDL levels which are thought to prevent atherosclerosis. Liver specific expression (i.e., transcriptional activation of the apoAI gene in liver cells) depends on synergistic interactions between transcription factors bound to three distinct sites, sites A(−214 to −192), B(−169 to −146) and C(−134 to −119), within a powerful liver specific enhancer located between nucleotides −222 to −110 upstream from the apoAI gene transcription start site (+1). Several members of the steroid/thyroid nuclear hormone receptor superfamily bind with high affinity to site A. In particular, the recently identified retinoic acid (RA) responsive receptor RXRα binds to site A either as a heterodimer with the retinoic acid receptors RARα, RARβ and RARγ or the orphan receptor ARP-1 in the absence of retinoids, or as a homodimer in the presence of 9-cis-RA. Alone, the previously characterized RAreceptors RARα and RARβ do not bind to site A. Thus, although site A responds selectively to RXRα over RARα and RARβ, it nevertheless binds efficiently to RXRα/RARα and RXRα/RARβ heterodimers.

In mammalian cells, RXRα activates transcription of nearby basal promoters from site A in the presence of low concentrations ($10^{-7}$M) of 9-cis-RA but not in response to similarly low concentrations of all-trans-retinoic acid (all-trans-RA). However, RXRα and RARα together can activate transcription in response to low concentrations of either 9-cis-RA or all-trans-RA. In contrast, the orphan receptor ARP-1 binds to site A and antagonizes this RXRα and RA dependent transactivation. Although these 5 observations raise the possibility that different retinoids activate transcription from site A via different homo- and heterodimeric versions of RARs, the presence of endogenous RARs in mammalian cells commonly used for these experiments precludes unequivocal elucidation of the specific signaling pathways involved.

Although 9-cis retinoic acid is a potent ligand for RXRα, retinoids have toxic side effects when used at high concentrations. Thus, the specific aims of the present invention are: (1) Development of a high throughput receptor-based screen to identify novel nontoxic ligands for the retinoid X receptor; and (2) Production of yeast recombinant retinoid X receptor for in vitro DNA-binding studies (gel shift assays), which can be exploited as a fast screening assay to identify new ligands for RXRα or to identify new factors which heterodimerize with RXRα.

It has been previously reported that the chicken progesterone receptor and the human Vitamin D3 receptor can be functionally expressed in yeast. It has not, however, been reported or suggested in the art that the retinoid X receptor can be expressed in yeast and, if expressed, can be useful for a screening method in which nontoxic agonists and antagonists of RXRα may be determinable.

BRIEF DESCRIPTION OF THE DRAWINGS

The background of the invention and its departure from the art will be further described hereinbelow with reference to the accompanying drawings, wherein:

FIG. 9 demonstrates that the sequence CCT in the spacer region between the two TGACC direct repeats in site A5' determines its selective responsiveness to RXRα and RA. A reporter construct similar to [A5']-41ALCAT but containing two copies of a mutated version of site A5' in which the sequence CCT in the spacer between the two repeats in the site A5' has been changed to TTT (M3) is tested for its responsiveness to different amounts (indicated) of the RXRα or RARα expression vectors in the presence of RA and the indicated amounts of the ARP-1 expression vector by transient transfection assays into CV-1 cells as described in FIG. 8. The data represent the average of at least two independent experiments.

SUMMARY OF THE INVENTION

The present invention relates to a novel screening method for the retinoid X receptor ("RXR") agonists or antagonists. The purpose of this method is to study and/or identify compounds which act as agonists and/or antagonists of retinoids. Further, the present invention also relates to the identification of RXRα selective target sites that are similar, but not identical, to a site, i.e., site A, which is involved in transcriptional activation of the apolipoprotein AI gene ("apoAI").

Specifically, a yeast-based expression system is used in the present invention thereby enhancing the ease and rapidity in which screening is accomplished. The expression of a fusion protein of the retinoid X receptor and a yeast ubiquitin fusion system is under the control of a constitutive yeast promoter, triosephosphate dehydrogenase (TDH$_3$). The receptors expressed in yeast cells exhibit hormone responsiveness with affinity and specificity characteristics of the authentic RXRα. Hormone-dependent transcriptional activation of the expressed receptor is determined by transforming yeast cells with a reporter plasmid that contains two copies of the apoAI site A element upstream of the yeast proximal CYC1 promoter fused to the lacZ gene of E. coli.

It is an object of the present invention, therefore, to provide a simple, economically attractive method to screen for retinoid agonists and/or antagonists. It is another object of the present invention to identify the critical transcriptional activity centers of the apolipoprotein AI gene. By utilizing the method of the present invention, derivatives of RXRα, such as heterodimers between RXRα and ARP-1, may be developed to produce new therapeutic compounds. Further purposes and objects of the present invention will appear as the specification proceeds. These and further objects of the invention are disclosed in the detailed description of the invention provided hereinbelow.

DETAILED DESCRIPTION OF THE INVENTION

In accordance with the present invention, the functional expression of the retinoid X receptor in yeast (Saccharomyces cerevisiae), mapping of site A of the apolipoprotein AI gene and a series of mutants of site A in yeast cells are provided to obtain a novel screen for identifying agonists and/or antagonists of RXRα. The goal of the screen is to express RXRα in yeast cells containing the retinoid X responsive reporter plasmid.

Figure 1A:
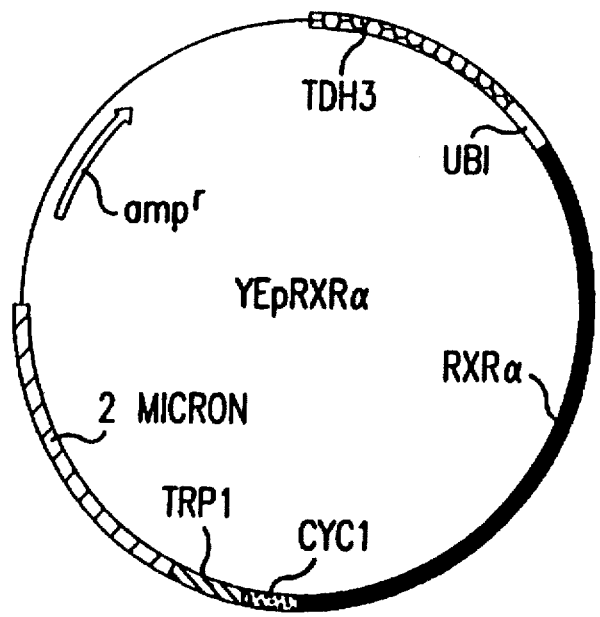
FIG. 1A shows the yeast expression plasmid for RXRα (YEpRXRα). The human RXRα coding sequence is inserted into the yeast expression vector to produce a ubiquitin (UBI)-fusion protein under the control of a constitutive promoter, triosephosphate dehydrogenase (TDH$_3$). TRP1 is the tryptophan selectable marker and 2 micron is the replicating yeast DNA.
Figure 1B:
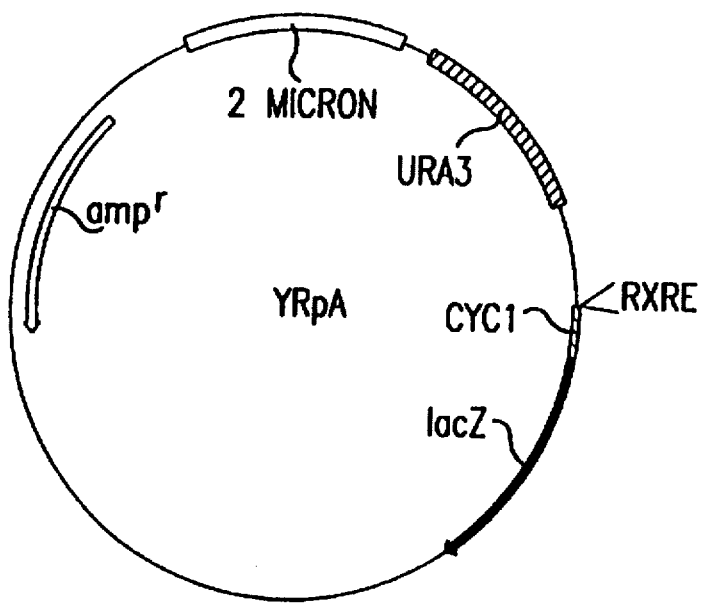
FIG. 1B shows the yeast reporter plasmid for RXRα (YEpA). An oligonucleotide containing two copies of site A as retinoid X response element (RXRE) is inserted into the unique XhoI site of the yeast reporter plasmid at the nucleotide position of −250 upstream of the iso-1-cytochrome C promoter, which is fused to the lacZ gene of $E.\ coli$. URA3 is the uracil selectable marker.
Figure 5:
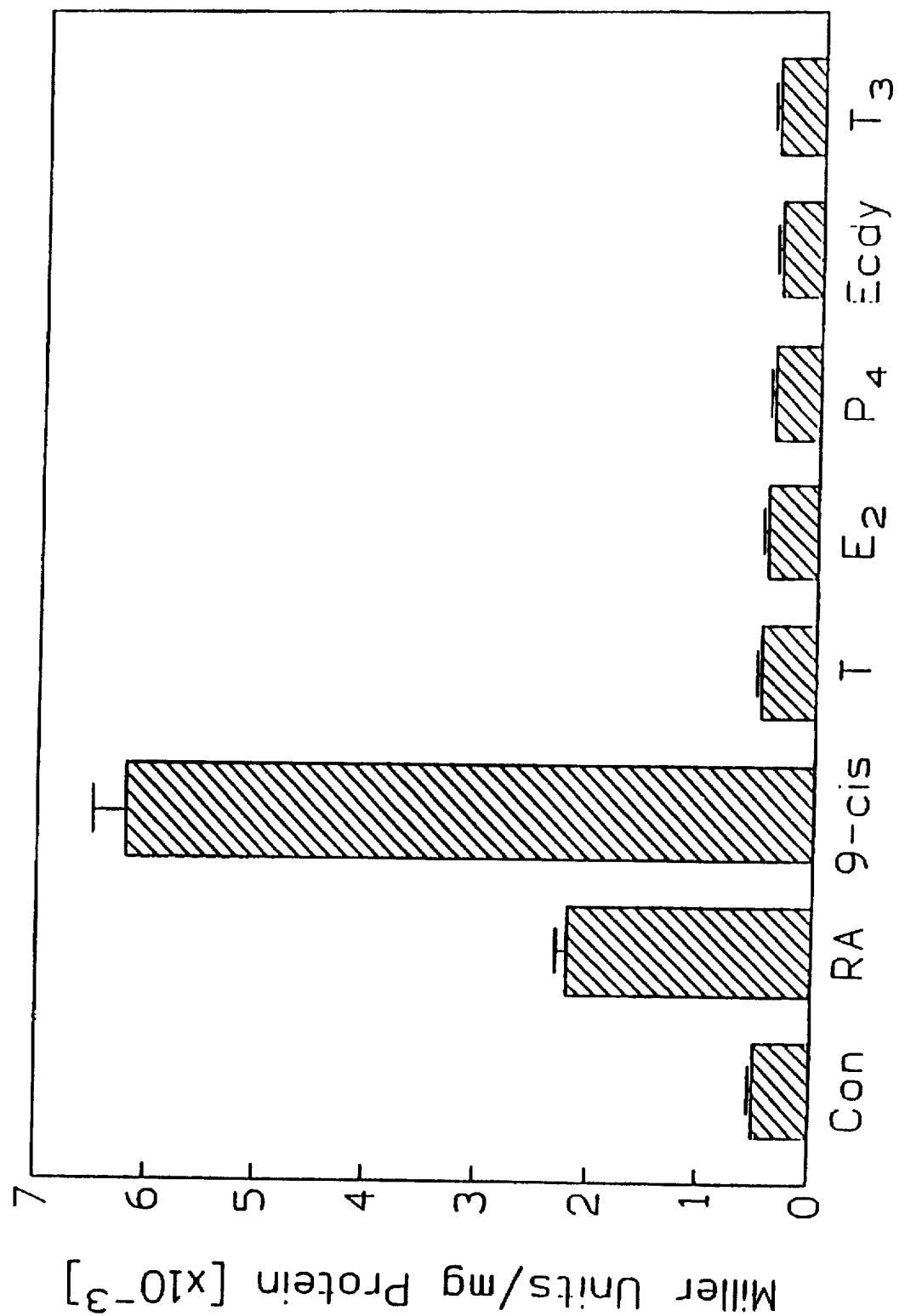
FIG. 5 describes the ligand-dependent transcriptional activation of RXRα in yeast. Yeast strains carrying the receptor and reporter plasmids (YEpRXRα/YRpA) are grown in medium containing $1 \times 10^{-6}$M each of either all-trans-retinoic acid (RA), 9-cis-retinoic acid (9-cis), testosterone (T), 17-β estradiol (E$_2$), progesterone (P$_4$), ecdysone (Ecdy), thyroid hormone (T$_3$) or no hormone (Con). Induction of β-galactosidase enzyme (Miller Units/mg) is measured in yeast extracts. Values represent three separate experiments with standard errors of mean indicated.
Figure 6:
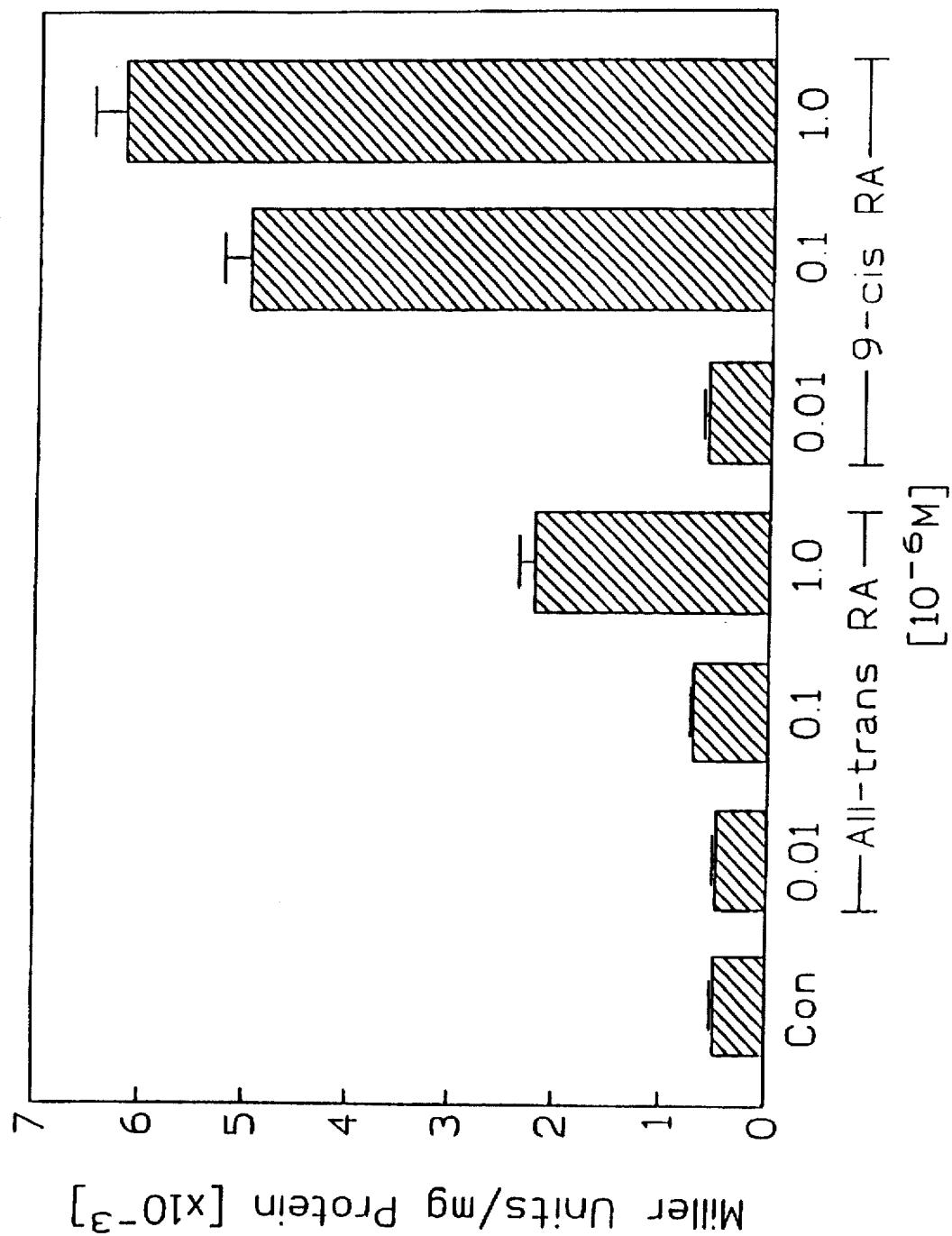
FIG. 6 refers to the dose-dependent nature of the retinoid responsive transcription unit in yeast. Yeast strains (YEpRXRα/YRpA) are grown in medium containing 0.01, 0.1 or $1.0 \times 10^{-6}$M of either all-trans-RA or 9-cis-RA. Control group (Con) contains no hormone. Induction of β-galactosidase enzyme (Miller Units/mg) is measured in yeast extracts. Values represent three separate experiments with standard errors of mean indicated.

The expression system described herein permits the development of a rapid method for screening for the agonists and/or the antagonists of the retinoid X receptor. Briefly, the yeast expression plasmid, YEpRXRα (FIG. 1A) is constructed to express RXRα as a ubiquitin fusion protein under the control of a constitutive yeast promoter, triosephosphate dehydrogenase (TDH$_3$). To study the transcriptional activation of the RXRα, yeast cells are cotransformed with the receptor expression plasmid (YEpRXRα) and the reporter plasmid (YRpA), which contain two copies of the apoAI gene site A upstream of the CYC1 promoter fused to the lacZ gene of E. coli (FIG. 1B). Hormone responsiveness is examined in these yeast transformants (YEpRXRα/YRpA) by measuring the induction of the reporter enzyme, β-galactosidase. As shown in FIG. 5, the transcriptional activation of RXRα in yeast cells is ligand-specific. The reporter enzyme can be induced by 9-cis retinoic acid (12–14 fold) and all-trans-retinoic acids (3–4 fold) whereas other hormones examined are not effective to activate the reporter gene. Thus, 9-cis retinoic acid ("9-cis-RA") is a potent inducer of RXRα mediated transactivation when compared to the all-trans-retinoic acids ("all-trans-RA") (FIG. 6). Consequently, functional expression of the RXRα receptor in yeast cells allows for the development of a high throughput screen (FIG. 7) to identify novel ligands, which can be exploited as potential therapeutic agents for atherosclerosis.

The present invention shows that RXRα expressed in yeast, which is devoid of endogenous RARs, binds efficiently to site A as a heterodimer with ARP-1 or RARα produced in mammalian cells in the absence of 9-cis-RA and as a homodimer in the presence of 9-cis-RA. It is also shown that these heterodimers bind to site A with an affinity significantly greater than the affinity of ARP-1 homodimer binding to the same site. Transcriptional activation assays in yeast show that in the presence of 9-cis-RA, but not in the presence of various steroids, thyroid hormone or all-trans-RA, RXRα transactivates efficiently a yeast basal promoter linked to site A. These findings indicate that RXRα homodimers bound to the apoAI gene site A respond selectively to 9-cis-RA in yeast, and function as transactivators recognized by the yeast basal transcription machinery. Furthermore, the present invention surprisingly shows that the mammalian RXRα and 9-cis-RA signaling system can be reconstituted in yeast.

An objective of this invention is to determine whether RXRα alone transactivates basal promoters from the apoAI gene site A in response to 9-cis-RA. Although in previous studies, it has been observed that site A responds preferentially to RXRα over the retinoic acid receptors RARα and RXRβ, the finding that RXRα forms heterodimers with RARα, RARβ, RXRγ and the orphan receptor ARP-1 that bind very efficiently to site A together with the observation that mammalian cells contain endogenous RARs and ARP-1 preclude unequivocal identification of the RXRα form (homo- or heterodimer) that activates site A in response to 9-cis-RA. Yeast does not seem to contain such endogenous receptors. If RXRα alone activates transcription from the apoAI gene site A, then it may be able to transactivate a yeast basal promoter linked to site A. Further experiments determine the choice of the yeast CYC1 basal promoter for the invention.

As a first step towards reconstitution of the RXRα and 9-cis-RA signaling system in yeast, it is determined whether RXRα can be produced in yeast using the yeast high copy number expression vector YEpRXRα (see FIG. 1A) in which the RXRα cDNA is placed under the control of the yeast constitutive promoter of the triosephosphate dehydrogenase gene (TDH3). Yeast transformants containing this vector are viable and crude extracts from these cells contain an activity that participates in formation of heterodimers with either ARP-1 or RARe which bind very efficiently to site A. In addition, while this activity alone is not capable of binding to site A, its binding seems to be enhanced by 9-cis-RA. However, binding in the presence of 9-cis-RA is relatively inefficient compared to binding of heterodimers with ARP-1 or RARα. The DNA binding properties of this activity are consistent with the properties of RXRα produced in mammalian cells indicating that RXRα is produced and it is stable in yeast. The observation that yeast produced RXRα in the presence of 9-cis-RA binds inefficiently to site A together with the finding that RXRα in RXRα/ARP-1 heterodimers does not participate in RXRα homodimer formation in the presence of 9-cis-RA suggest that RXRα produced in yeast binds to site A in two mutually exclusive modes. One, in the presence of 9-cis-RA, RXRα binds as a homodimer which is resistant to conversion to heterodimers in the presence of ARP-1 or RARα, and another, in the absence of 9-cis-RA but in the presence of ARP-1 or RARα, RXRα binds as a heterodimer which is resistant to conversion to homodimers in the presence of 9-cis-RA.

Transcription activation assays show that in the presence of 9-cis-RA, RXRe transactivates the yeast CYC1 basal promoter from the apoAI gene site A in yeast cells. This is a highly specific response because it does not occur in the absence of 9-cis-RA or in the presence of many different steroid/thyroid hormone ligands. The relatively low level of transactivation with high concentrations of all-trans-RA may reflect the presence of isomerases in yeast that convert RA to 9-cis-RA or, more likely, photochemical isomerization of RA to 9-cis-RA.

Figure 7:
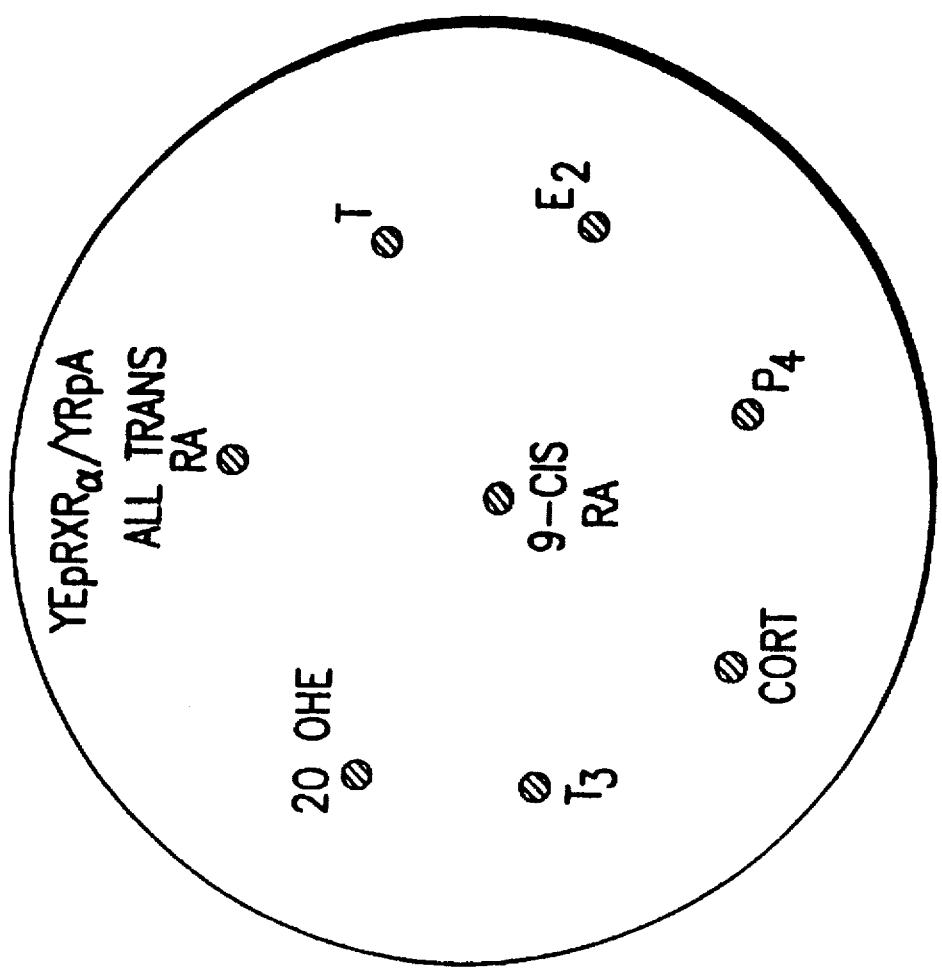
FIG. 7 shows a plate assay as a screen to detect RXRα agonists. Yeast cells containing the RXRα expression plasmid and the reporter construct are inoculated in Yeast media containing the chromogenic substrate, X-GAL® (a registered trademark of 5-bromo-4-chloro-3-indolyl-β-D-galactopyranoside, commercially available from Gibco BRL, Bethesda, Md.). Discs containing different hormones (all-trans-retinoic acid (ALL TRANS RA), 9-cis-retinoic acid (9-CIS RA), testosterone (T), 17-β estradiol (E$_2$), progesterone (P$_4$), thyroid hormone (T$_3$), cortisone (Cort) and 20-hydroxyecdysone (20OHE)) are placed on top of the agar plate. Induction of the reporter enzyme as reflected by the formation of the blue halo is observed for 9-cis retinoic acid and all-trans-retinoic acids only.

To identify nontoxic ligands of RXRα, the present invention includes a novel screen for detecting compounds having retinoid X receptor agonist or antagonist activity by the following steps: (1) Providing a yeast strain which expresses the retinoic acid receptor and activates the reporter plasmid containing apoAI gene site A or a mutated variant thereof; (2) incubating the compound in suitable media and a colorless chromogenic substrate; and (3) examining the media for development of color. FIG. 7 illustrates the screen as a plate assay which detects RXRα agonists. Yeast cells containing the RXRα expression plasmid and the reporter construct are inoculated in yeast media containing the chromogenic substrate, X-GAL® (a registered trademark of 5-bromo-4-chloro-3-indolyl-β-D-galactopyranoside, commercially available from Gibco BRL, Bethesda, Md.). Other well-known chromogenic substrates may substitute for X-GAL®. Then, discs containing different test compounds may be placed on top of the agar plate. Induction of the reporter enzyme by the ligands of RXRα is reflected by the formation of a color.

Site A is a specialized RA responsive element that responds preferentially to RXRα over RARα or RARβ. The current invention showing that site A can be transactivated efficiently by RXRα alone in the presence of 9-cis-RA confirm that site A is a target for transactivation by RXRα alone. Although this does not exclude the possibility that site A can also be transactivated by RXRα/RARα or RXRα/RARβ heterodimers, it shows clearly that RXRα can function as a transactivator on its own. The importance of site A in this transactivation is exemplified by the recent observation that similar experiments using an RA responsive element from the RARβ gene (βRARE) show that neither RXRα nor RARα alone can activate transcription from this element in yeast and that the presence of both RXRα and RARα is required for transactivation. It is therefore clear that different RA receptor heterodimeric combinations can function as transactivators only in conjunction with specific RA responsive elements.

The present invention demonstrates that RXRα can be produced and is stable in yeast, and that it is biologically active in transactivation of the yeast basal transcription machinery from the apoAI gene site A. This system allows for the genetic dissection of this retinoid signaling pathway in yeast and the identification of other retinoids and retinoid mimics capable of transactivating genes via this pathway. Such agents may be useful for raising apoAI and HDL plasma levels and for prevention or regression of atherosclerosis.

While the examples illustrate yeast and bacteria, it is contemplated that the invention may utilize any prokaryotic or eukaryotic host cell stably transformed or transfected by the expression vector containing a cDNA sequence which encodes a retinoid X receptor or the reporter plasmid containing apolipoprotein AI gene site A or a mutated variant thereof. Other host cells which may be adequate in the practice of this invention are well-known to those persons having ordinary skill in the art. Additionally, the invention encompasses the "biologically active equivalents" of the yeast and bacterial strains disclosed herein. These equivalents would include the natural mutations of the strains (e.g., spontaneous mutations) as well as the artificial mutations (e.g., mutations induced by conventional techniques within the ordinary skill of the art) whereby the mutants retain the ability to carry the expression vector and the reporter plasmid of the invention.

In the present invention, it is further found that multiple mechanisms integrate signals influencing apolipoprotein AI gene transcription in mammalian cells. The ability of site A to respond to various members of the steroid/thyroid receptor superfamily is evaluated by transient transfection assays in CV-1 cells. It is contemplated that expression vectors may similarly be constructed in yeast.

The results show that in addition to RXRα and retinoic acid, site A also responds efficiently to the orphan receptor HNF4, but it responds only weakly or not at all to the RARα, RARβ, thyroid hormone receptor, estrogen receptor and andogen receptor in the presence or absence of their corresponding ligands or to the orphan receptors ARP-1 and EAR3-COUP-TF. However, despite their ineffectiveness in stimulating expression from site A, some, but not all of these receptors alter the magnitude of transactivation of site A by RXRα and RA or by HNF4.

Mutational mapping analysis of site A reveals that only a short subregion of site A (site A5') sequence composed of two TGACC imperfect direct repeats separated by the trinucleotide spacer CCT is sufficient for transactivation by either RXRα and RA or HNF4. Transactivation by RXRα and RA is highly sensitive to nucleotide substitutions in these repeats, the number of nucleotides in the spacer and the sequence in the spacer. Similar experiments have been performed to show that transactivation by HNF4, another member of the nuclear hormone receptor superfamily, is relatively insensitive to all these nucleotide changes.

Remarkably, replacement of the spacer CCT in site A by TTT switches selective transactivation from RXRα and RA to RARα and RA. These unexpected findings suggest that during its evolution, site A has established and preserved critical structural requirements for selective recognition and transactivation by RXRα and RA while accommodating structural adaptations required for binding and transactivation by HNF4. Thus, mutated variants of site A may be used in the yeast system hereindescribed as a screen for identifying agonists and antagonists selectively for RXRα/ARP-1 heterodimers and HNF4.

The restriction enzymes, T4 polynucleotide kinase and T4 DNA ligase used in the following examples are purchased from New England Biolabs. Calf intestinal alkaline phosphatase is purchased from United States Biochemical Corporation. Taq polymerase is bought from Perkin-Elmer Cetus. Radioinert steroids, cyproterone acetate adenine sulfate, o-nitrophenyl β-D-galactopyranoside and uracil are acquired from Sigma. Casamino acids, yeast nitrogen base and dextrose are purchased from Difco. Glassperlen is bought from B. Braun Melsungen AG. The alkaline phosphatase conjugate immunoblot assay kit is purchased from BioRad. All-trans-retinoic acid is purchased from Sigma and dissolved in DMSO at stock concentration of $10^{-3}$M.

For ease in reviewing the examples, the following is provided: The homogenization buffer employed in the illustrations of the invention contains 10 mM Tris, 0.1 mM EDTA, 2 mM dithiothreitol and 10% glycerol, pH 8.1 at room temperature (TEDG buffer). The transcription buffer for β-galactosidase assay contains 0.12M sodium phosphate (dibasic), 0.04M sodium phosphate (monobasic), 10 mM potassium chloride, 1 mM magnesium sulfate and 0.27% 2-mercaptoethanol, pH 7.0 at room temperature.

Finally, the *Saccharomyces cerevisiae* strain used in the present invention is BJ3505 (Matα pep4::his3 PR61-Δ1.6R his3lys2-208trp1-Δ101 ura3-52 gal2) obtained from that source. Expression of the retinoid X receptor is under the control of a constitutive yeast promoter, triosephosphate dehydrogenase (TDH3). Growth and transformation of yeast cells is performed according to standard procedures.

Briefly, yeast cells are grown in 10 mL of YEPD medium overnight at 30° C. until cell density reaches an O.D. of 1.0. Cells are then collected by centrifugation and washed with 10 mL of 0.1M lithium acetate. Cells are then resuspended in 10 mL 0.1M lithium acetate and incubated at 30° C. for 1 hour. Cells are collected and resuspended in 0.5 mL 0.1M lithium acetate. Aliquots of cells (50 mL) are incubated with 1–2 mg DNA and incubated for 10 minutes at 30° C. followed by 1 hour incubation in the presence of 0.5 mL 40% polyethyleneglycol (4000). The cell mixture is heated for 5 minutes at 42° C. Cells are then collected and plated onto appropriate yeast media. Transformants are selected by tryptophan auxotrophy.

The plasmids, DNA sequences and microorganisms deposited in connection with the present patent application, except where specified to the contrary, are deposited in American Cyanamid Company's culture collection maintained in Princeton, N.J. and are deposited pursuant to the Budapest Treaty with the American Type Culture Collection (ATCC) in Rockville, Md. 20952, U.S.A.

The *E. coli* bacterial strains (DH5α) which were deposited in the ATCC on Dec. 3, 1992 include the strains carrying the expression vector and reporter plasmid YEpRXRα (ATCC 69145) and YRpA (ATCC 69144), respectively. The *Saccharomyces cerevisiae* yeast strains which were deposited in the ATCC on Dec. 3, 1992 include the strains carrying the reporter plasmid, the expression vector/reporter plasmid BJ YRpA (ATCC 74195), BJ YEpRXRα/YRpA (ATCC 74196) and BJ YEpRXRα (ATCC 74197), respectively. The *E. coli* bacterial strains (HB101) which were deposited in the ATCC on Dec. 22, 1992 include the strains carrying the reporter plasmids [M3]-41ALCAT (ATCC 69168), [M6]-41ALCAT (ATCC 69169), [M4]-41AI.CAT (ATCC 69170) and [A5']-41ALCAT (ATCC 69171).

A further understanding of the present invention can be obtained from the following examples. However, the examples are set forth only for the illustration of certain aspects of the invention and are not to be construed as limitations thereon. Unless otherwise expressed, all parts are by weight.

EXAMPLE 1

Construction of Yeast Expression Vector for Retinoid X Receptor (RXRα)

Two unique restriction sites are engineered at the 5' and 3' ends of the RXRα coding sequence for insertion into the yeast expression vector (YEpV5). This is achieved by PCR-mediated mutagenesis. The first two primers used to amplify the N-terminal portion of the gene (658 bp) are:

5'-TACGGCCGATGGACACCAAACATTTC-CTG-3' (SEQ ID NO:1)

5'-TAGTCGACTCCACCTCATTCTCGTTCCG-3' (SEQ ID NO:2)

The resulting 658 base pairs fragment contains an EagI site in front of the start codon and an AccI site at the C-terminus. The second set of primers used to amplify the other half of the RXRα gene (729 bp) are:

5'-ATGTCGACCAGCAGCGCCAACGAGGAC-3' (SEQ ID NO:3)

5'-TACACACAGTGCTAACTCATTTGGTGCGG-CGCCTC-3' (SEQ ID NO:4)

The resulting 729 base pairs PCR fragment contains an AccI site at the 5' end and a DraIII site right after the stop codon. In order to produce an in frame ubiquitin-fusion receptor protein under the control of a constitutive yeast promoter (TDH$_3$), an oligonucleotide containing an EagI and a DraIII site is inserted into the AflII-KpnI sites of the yeast expression vector (YEpV5). After complete digestion with EagI and DraIII, the expression vector is ligated to the 658 base pairs and the 729 base pairs PCR fragments of the RXRα receptor. The resulting receptor expression vector (YEpRXRα) (FIG. 1A) is used to transform Trp-1 deleted yeast strain, BJ3515, using conventional lithium acetate protocol. Transformants are selected by tryptophan auxotrophy.

EXAMPLE 2

Construction of Reporter Plasmid

Two copies of an oligonucleotide containing the apoAI gene site A which has been shown to function as retinoic acid response element in mammalian cells is cloned into the unique XhoI site of the yeast reporter plasmid YRpPC2. The resulting reporter plasmid (YRpA) (FIG. 1B) contains the two copies of site A at nucleotide position −250 upstream of the iso-1-cytochrome C (CYC1) promoter which is fused to the β-galactosidase gene of E. coli. This reporter is used to transform yeast cells expressing the RXRα receptor (YEpRXRα). The double transformant yeast cells (YEpRXRα/YRpA) are selected by tryptophan and uracil auxotrophy.

EXAMPLE 3

Preparation of Yeast Extracts (YEpRXRα)

Yeast cells containing the RXRα receptor expression construct (YEpRXRα) are grown overnight at 30° C. in minimal medium (2% dextrose, 0.1% casamino acids, 0.67% yeast nitrogen base, 0.001% adenine and 0.002% uracil). When cell density reaches late-log phase, cells are harvested and washed with receptor buffer (TEDG). This and all subsequent steps are done at 4° C. The final cell pellets are suspended in TEDG buffer and mixed with an equal volume of glass beads. Cells are disrupted by vortexing. The homogenate is centrifuged at 100,000×g for 30 minutes to obtain yeast extracts which are used for gel retardation assays. Protein concentration is determined by Bio-Rad protein assay according to the manufacturer's published protocol using bovine serum albumin as standard.

EXAMPLE 4

Electrophoretic Mobility Shift Assays (EMSA)

EMSA are performed using a $^{32}$P-labeled double stranded oligonucleotide with a sequence corresponding to the apoAI gene site A (oligo A probe). 40 μg of yeast extract is used in all binding reactions except in the 9-cis-RA experiment in which 60 μg extract is used. When 9-cis-RA is used ($5\times10^{-5}$M), it is preincubated with yeast extracts at room temperature for 20 minutes before addition of the probe. All receptors are produced by transfecting CMT cells which are similar to Cos-1 cells with various expression plasmids including pMT2-ARP-1, pMT2-ARPΔA1, pMT2-ARPΔA6, pMT2-ARPΔA7 and pMT2-RARα. Mixtures of yeast and CMT cell extracts contain 2 μg of CMT cell extracts. Protein-DNA complexes are analyzed by 6% non-denaturing polyacrylamide gel by conventional procedures.

EXAMPLE 5

Preparation of 9-cis-Retinoic Acid

In 20 mL of 50% ethanol/water, 100 mg of 9-cis-retinal is dissolved in a capped vial wrapped with aluminum foil. After 200 mg of NaOH and 450 mg of AgNO$_3$ is added, the vial is shaken vigorously at room temperature for at least 24 hours until disappearance of the starting retinal. Reaction is followed by HPLC (Vedec C18 column; MeCN/0.1% TFA gradient; 75–85%; 10 minutes, 1 mL/minute, 350 nm, retention time; 10.4 minutes for 9-cis-retinoic acid, and 11.6 minutes for all-trans). Greater than 90% of the products are 9-cis-retinoic acid.

For purification, the reaction mixture is acidified by adding acetic acid and 5 mL of water and then filtered with 0.45μ Whatman disk. The filtrate is pumped through a 900 mg C18 cartridge. 9-cis-retinoic acid is retained on the column. The column is then desalted with a water wash (40 mL). The retinoic acid is washed out with MeOH/MeCN (2:1). The product is concentrated under reduced pressure to dryness. Yield is about 25 mg of title product (25% yield).

EXAMPLE 6

Transcription Assays

Yeast strains containing the RXRα receptor expression construct and the reporter plasmid (YEpRXRα/YRpA) are grown in minimal medium (without tryptophan and uracil) in the absence or presence of all-trans-RA, 9-cis-RA or other steroid hormones. When cells reach late-log phase, yeast extracts are prepared and assayed for β-galactosidase activity.

EXAMPLE 7

Efficient Binding of Yeast Cell Produced RXRα to the apoAI Gene Site A as a Heterodimer with Mammalian Cell Produced ARP-1 or RARα

Figure 2:
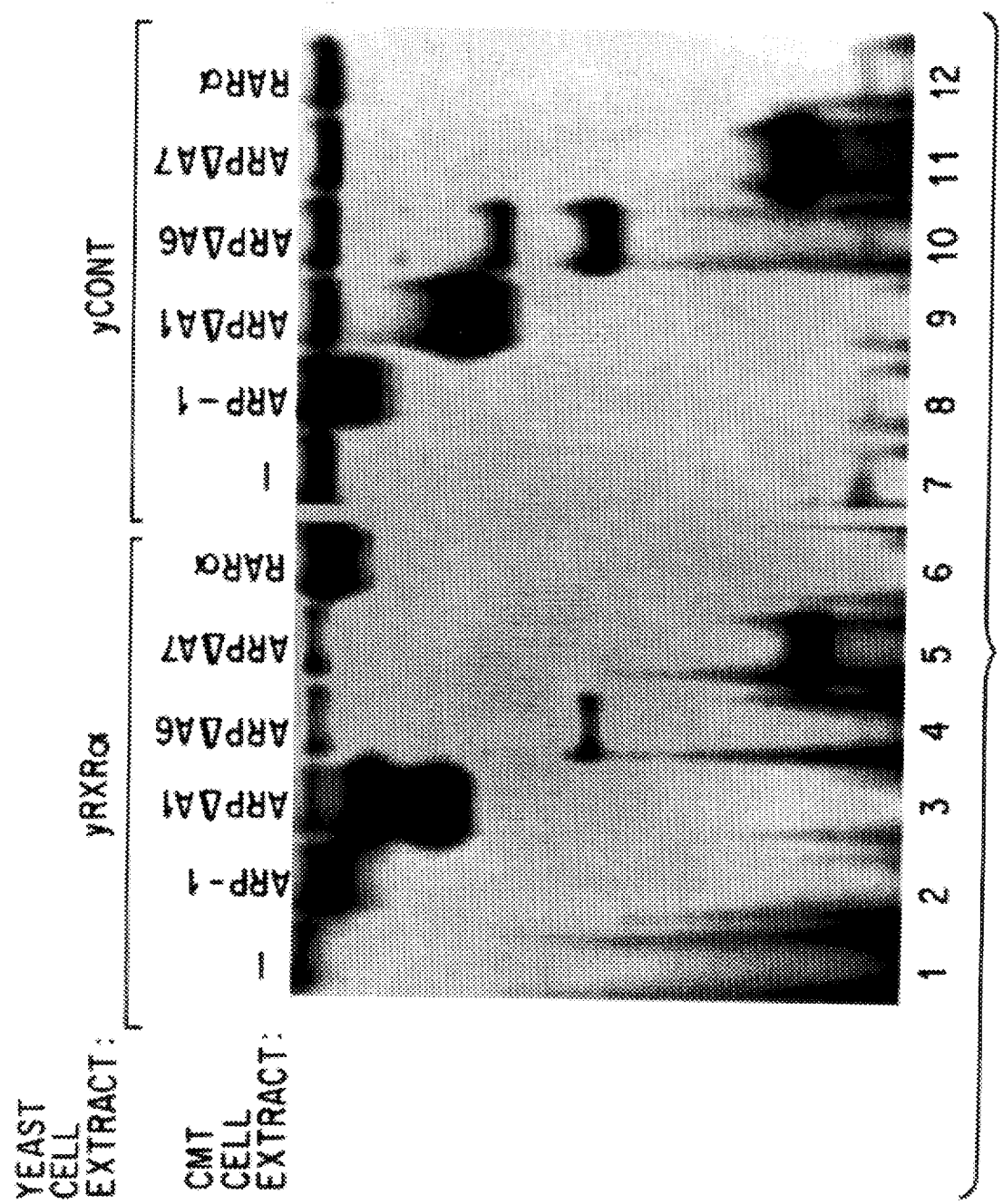
FIG. 2 shows that the RXRα produced in yeast heterodimerizes with ARP-1 and RARα produced in mammalian cells. Extracts (40 μg) from yeast cells producing RXRα (yRXRα extracts, lanes 1–6) and from untransfected yeast control cells (yCONT, lanes 7–12) are mixed with extracts (2 μg) from untransfected CMT cells (lanes 1 and 7) or from CMT cells transfected with vectors expressing ARP-1 (lanes 2 and 8), ARPΔA1 (lanes 3 and 9), ARPΔA6 (lanes 4 and 10), ARPΔA7 (lanes 5 and 11) or RARα (lanes 6 and 12) and the mixtures are analyzed by EMSA using $^{32}$P-labeled oligo A as a probe. The resulting autoradiogram is shown.

In previous studies it has been observed that while Cos-1 cell produced RXRα binds with low affinity to the apoAI gene site A, mixing of Cos-1 cell produced RXRα with Cos-1 cell produced ARP-1, RARα or RXRβ results in formation of RXRα/ARP-1, RXRα/RARα or RXRα/RARβ heterodimers which bind with very high affinity to the same site. To determine whether yeast produced RXRα can also form heterodimers with ARP-1 or RARα that bind efficiently to site A, crude extracts prepared either from yeast cells containing the RXRα yeast expression vector YEpRXRα (yRXRα extracts) or from untransformed yeast control cells (yCONT extracts) are mixed with whole cell extracts from CMT cells transiently transfected with mammalian cell expression vectors expressing ARP-1, various ARP-1 deletion mutants (see below) or RARα. The ARP-1 deletion mutants are ARPΔA1, ARPΔA6 and ARPΔA7 all of which contain the ARP-1 DNA binding domain. ARPΔA1 lacks the ARP-1 amino-terminal domain, ARPΔA6 lacks the ARP-1 carboxy-terminal domain, and ARPΔA7 lacks both the amino- and carboxy-terminal domains. These extract mixtures are then tested for binding to site A by EMSA using as a probe a $^{32}$P-labeled double stranded oligonucleotide with a sequence corresponding to the apoAI gene site A (oligo A probe). The results in FIG. 2 show that either yRXRα or yCONT extracts mixed with extracts from untransfected CMT cells form faint retardation complexes with similar electrophoretic mobilities which are most likely due to endogenous yeast factors (lanes 1 and 7). yRXRα or yCONT extracts mixed with extracts from CMT cells transfected with the ARP-1 expression vector form intense slow migrating retardation complexes with similar electrophoretic mobilities (lanes 2 and 8). yRXRα extracts mixed with extracts from CMT cells transfected with the ARPΔA1 expression vector, on the other hand, form two relatively faster migrating complexes while yCONT extracts mixed with the same CMT cell extracts form only one complex with an electrophoretic mobility similar to the faster migrating complex formed with yRXRα and these CMT cell extracts (compare lanes 3 and 9). yRXRα or yCONT extracts mixed with extracts from CMT cells transfected with the ARPΔA6 expression vector form even faster migrating retardation complexes with similar electrophoretic mobilities (lanes 4 and 10) and yRXRα or yCONT extracts mixed with extracts from CMT cells transfected with the ARPΔA7 expression vector form very fast migrating complexes with similar electrophoretic mobilities (lanes 5 and 11). Finally, yRXRα extracts mixed with extracts from CMT cells transfected with the RARα expression vector form an intense, relatively diffuse, slow migrating retardation complex, while yCONT extracts mixed with the same CMT cell extracts do not form this retardation complex (compare lanes 6 and 12).

These results indicate that similar to RXRα produced in mammalian cells, RXRα produced in yeast cells does not bind to the apoAI gene site A but forms heterodimers with mammalian cell produced ARP-1 or RARα that bind very efficiently to the same site. Furthermore, these results indicate that the ARP-1 carboxy-terminal domain plays a determinant role in formation of these RXRα/ARP-1 heterodimers, but not the ARP-1 amino-terminal domain nor the ARP-1 DNA binding domain.

EXAMPLE 8

Figure 3:
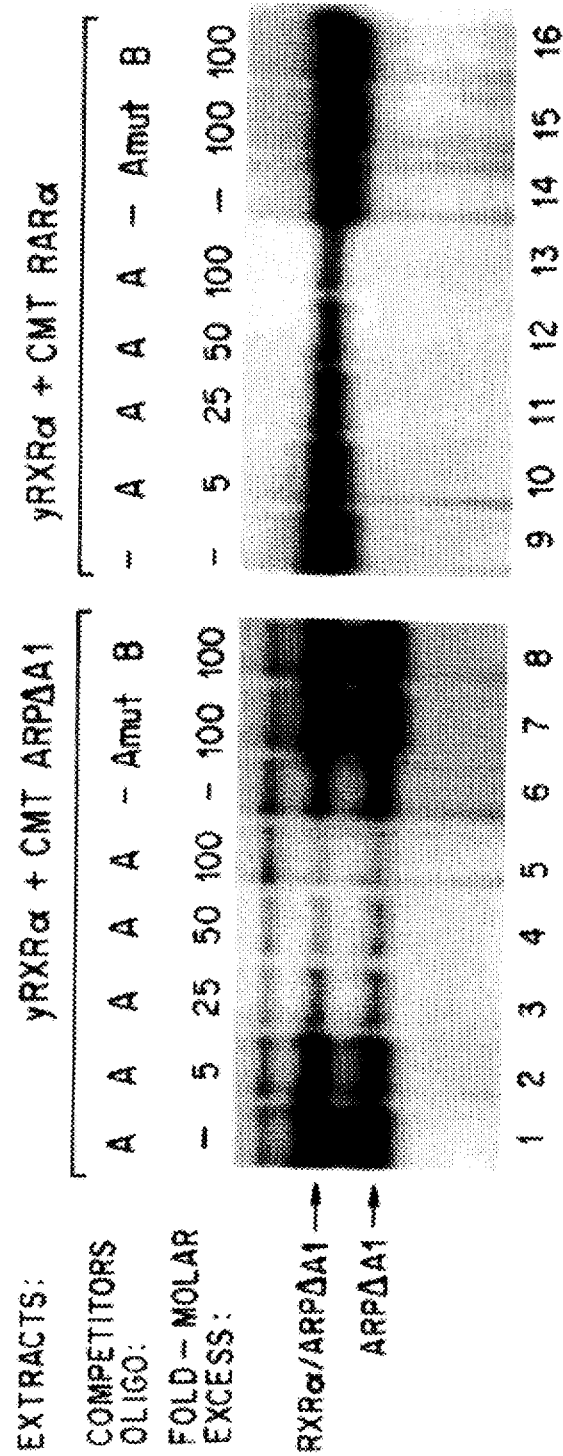
FIG. 3 demonstrates that the heterodimers between yeast produced RXRα and CMT cell produced ARP-1 or RARα bind with high affinity and specificity to site A. Extracts (40 μg from yeast cells producing RXRα (yRXRα lanes 1–16) are mixed with extracts from CMT cells transfected with vector expressing either ARPΔA1 (lanes 1–8) or RARα (lanes 9–16) and are analyzed by EMSA with $^{32}$P-labeled oligo A as a probe in the presence of the indicated fold-molar excess of unlabeled oligo A (A), oligo Amut (Amut) or oligo B (B). RXRα/ARPΔA1 heterodimers and ARPΔA1 homodimers are indicated by arrows on the left, and RXRα/RARα homodimers by an arrow on the right.

Binding of Heterodimers Between Yeast Cell Produced RXRα and Mammalian Cell Produced ARP-1 or RARα to the apoAI Gene Site A with High Affinity and Sequence Specificity It has been previously observed that RXRα/ARP-1 heterodimers formed with RXRα and ARP-1 produced in Cos-1 cells bind to the apoAI gene site A with an affinity approximately ten times greater than the affinity of binding of either ARP-1 or RXRα alone to the same site. The affinity of RXRα/ARP-1 and RXRα/RARα heterodimers formed with yeast produced RXRα and CMT cell produced ARP-1 or RARα for site A, relative to the affinity of the CMT cell produced ARP-1 for the same site, is evaluated by competition EMSA. Specifically, yRXRα extracts are mixed with either CMT cell produced ARPΔA1 or CMT cell produced RARα and the mixtures are used for EMSA with the oligo A probe in the presence of increasing amounts of unlabeled oligo A. The results in FIG. 3 show that while ARPΔA1 binding is effectively eliminated with 25-fold molar excess of unlabeled oligo A over the oligo A probe (lane 3), elimination of either the RXRα/ARPΔA1 or the RXRα/RARα heterodimers requires at least 50-fold molar excess of unlabeled oligo A over the oligo A probe (lanes 4, 5, 12 and 13). Similar competition EMSA experiments using as competitors a mutated version of site A (oligo Amut), or an oligonucleotide with a sequence corresponding to a different region of the apoAI gene promoter (oligo B) show that these competitors do not affect binding of either ARPΔA1, RXRα/ARPΔA1 or RXRα/RARα heterodimer binding to site A (lanes 7, 8, 15 and 16).

These results indicate that similar to heterodimers between RXRα and ARP-1 or RARα produced in mammalian cells, heterodimers between yeast cell produced RXRα and mammalian cell produced ARP-1 or RARα bind to the apoAI gene site A with high sequence specificity and an affinity significantly greater than the affinity of binding of ARP-1 produced in mammalian cells for the same site.

EXAMPLE 9

Figure 4:
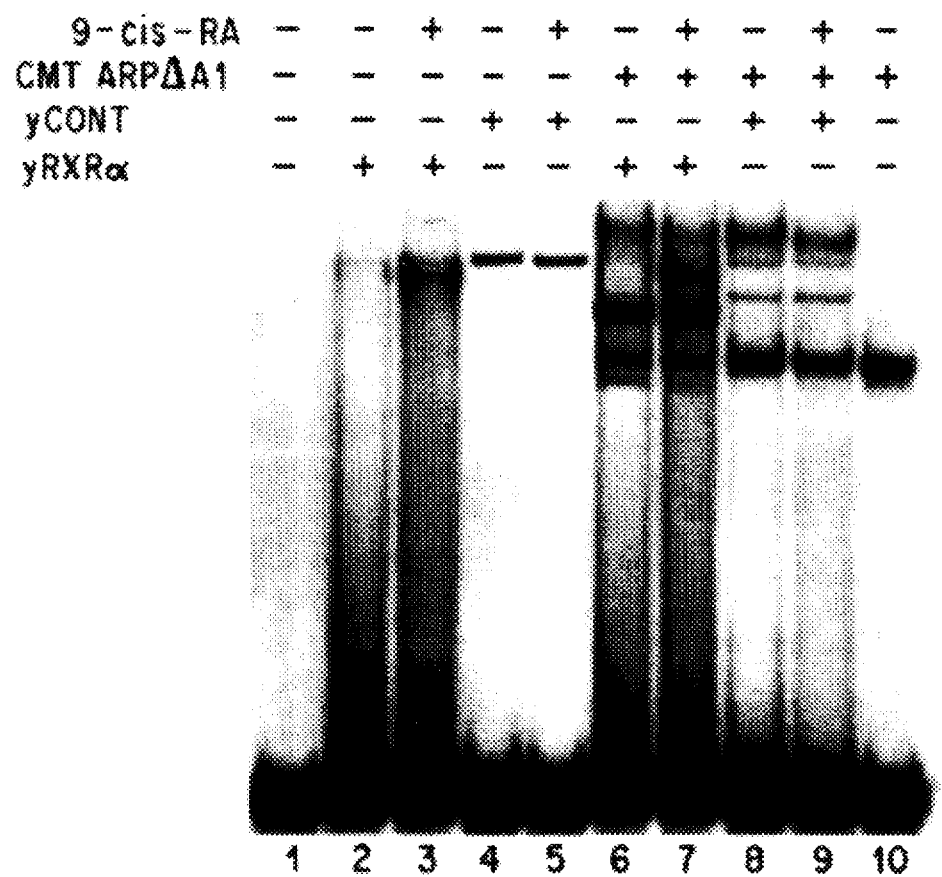
FIG. 4 illustrates that RXRα produced in yeast binds to site A as a homodimer in the presence of 9-cis-RA. Extracts (60 μg) from yeast cells producing RXRα (yRXRα, lanes 2, 3, 6 and 7) and from yeast control cells (yCONT, lanes 4, 5, 8 and 9) are analyzed by EMSA using $^{32}$P-labeled oligo A as a probe after mixing with extracts (2 µg) from untransfected CMT cells (lanes 1–5) or from CMT cells transfected with a vector expression ARPΔA1 (lanes 6–10) in the presence (lanes 3, 5, 7 and 9) or absence (lanes 1, 2, 4, 6, 8 and 10) of $5 \times 10^{-5}$M 9-cis-RA.

Binding of Yeast Produced RXRα to the apoAI Gene Site A in the Presence of 9-cis-RA It has been recently reported that RXRα prepared by translation of RXRα mRNA in reticulocyte lysates in vitro does not bind to the apoAI gene site A unless these lysates are supplemented with either cell extracts or 9-cis-RA and to the lesser extent with all-trans-RA. To determine whether yeast produced RXRα binds to site A in the presence of 9-cis-RA, yRXRα and the control yCONT extracts are tested for binding to the oligo A probe in the presence or absence of $5\times10^{-5}$M 9-cis-RA by EMSA. The results in FIG. 4 show that compared with the electrophoretic migration of the probe in the absence of any extracts (lane 1) the probe incubated with the yRXRα extracts migrates as a smear of multiple retardation complexes in the absence of 9-cis-RA (lane 2). In the presence of 9-cis-RA, however, the probe migrates as a distinct retardation complex (lane 3) easily distinguishable from the retardation complex, due to the endogenous yeast factors which is also observed with yCONT extracts in the absence (lane 4) or in the presence (lane 5) of 9-cis-RA. The retardation complex observed with yRXRα extracts in the presence of 9-cis-RA is specific for the oligo A probe because it is efficiently competed by a 50-fold molar excess of unlabeled oligo A but not by a 100-fold molar excess of a mutated version of oligo A (oligo Amut) which neither binds RXRα nor is it transactivated by RXRα and RA in mammalian cells. However, formation of this complex seems to be relatively inefficient compared to the formation of yRXRα/ARP-1 and yRXRα/RARα complexes (compare FIG. 4, lane 3 with FIG. 2, lanes 3 and 6).

These results indicate that similar to RXRα produced by in vitro translation of RXRα mRNA, yeast produced RXRα binds to the apoAI site A as a homodimer in the presence of 9-cis-RA. This, together with the observation that RXRα also binds to site A as a heterodimer with ARP-1 or RARα in the absence of 9-cis-RA raise the possibility that in vitro the ratio of the intracellular concentrations of retinoids, ARP-1 and RARα may play a fundamental role in determining whether site A is occupied by RXRα homodimers or heterodimers.

EXAMPLE 10

Attempt to Form RXRα Homodimers By RXRα in RXRα/ARP-1 Heterodimers in Response to 9-cis-RA To determine whether RXRα in RXRα/ARP-1 heterodimers can in the presence of 9-cis-RA participate in the formation of RXRα homodimers, ARPΔA1 containing CMT cell extracts is mixed with either yRXRα or yCONT extracts and their binding to oligo A probe in the absence or the presence of 9-cis-RA is tested by EMSA. The results in FIG. 4 show that in the absence of 9-cis-RA, the CMT ARPAA1 and yRXRα yeast cell extract mixture forms three retardation complexes; one due to the endogenous yeast factors (see, for example, lanes 4 and 5), another due to ARPΔA1 (see, for example, lane 10), and a third retardation complex between them due to RXRα/ARPAA1 heterodimers (lane 6). In the presence of 9-cis-RA, although this pattern of retardation complexes remains unchanged, a new retardation complex migrating between that due to the yeast endogenous proteins and that due to RXRα/ARPΔA1 heterodimers also appears (compare lanes 3 and 7). This new retardation complex migrates at the same position as that observed with yRXRα extracts in the presence of 9-cis-RA (compare lanes 3 and 7) and thus most likely represents RXRα homodimers. None of the retardation complexes between those due to the endogenous yeast proteins and those due to ARPΔA1 are observed when the same experiment is repeated using yCONT extracts instead of RXRα extracts in the absence (lane 8) or the presence (lane 9) of 9-cis-RA.

These results indicate that although RXRα binds to the apoAI gene site A either as a homodimer in the presence of 9-cis-RA, or as a heterodimer with ARP-1 in the absence of 9-cis-RA, RXRα in these heterodimers is unresponsive to 9-cis-RA in formation of RXRα homodimers. In other words, RXRα in RXRα/ARP-1 heterodimers does not form RXRα homodimers in response to 9-cis-RA. Furthermore, since in the presence of excess ARPΔA1 not all yeast RXRα is converted into RXRα/ARPΔA1 heterodimers, but a portion of it remains responsive to 9-cis-RA for formation of homodimers, yeast produced RXRα appears to be distributed into two distinct and separate pools: One capable of homodimerization in the presence of 9-cis-RA but incapable of heterodimerization with ARP-1, and another capable of heterodimerization with ARP-1 but incapable of forming homodimers in response to 9-cis-RA.

EXAMPLE 11

Transactivation by RXRα of a Yeast Basal Promoter Linked to the apoAI Gene Site A in Response to Retinoids To determine whether the RXRα produced in yeast can be recognized by the yeast basal transcription machinery and activate transcription from yeast basal promoters, a reporter plasmid containing two copies of the apoAI gene site A upstream of the yeast proximal iso-1-cytochrome C (CYC1) promoter fused to the *E. coli* lacZ gene is constructed. The resulting reporter construct (YRpA) is used to transform yeast cells containing the RXRα expression vector YEpRXRα and the resulting transformed yeast cells (YEpRXRα/YRpA) are tested for their ability to express the lacZ gene product, β-galactosidase (β-gal), in the absence of any ligands (Con) and in the presence of $10^{-6}$M of all-trans-RA (RA), 9-cis-RA (9-Cis), testosterone (T), estradiol ($E_2$), progesterone ($P_4$), ecdysone (Ecdy) and thyroid hormone ($T_3$). The results in FIG. 5 show that cells treated with 9-cis-Ra or all-trans-RA express 14- and 4-fold greater amounts of β-gal activity compared to control (Con) cells. In contrast, cells treated with all other ligands express β-gal activity at amounts comparable to that expressed by control cells.

These results, together with the results of the previous examples, strongly suggest that RXRα in yeast cells binds to the apoAI gene site A and stimulates transcription from nearby yeast basal promoters specifically in response to treatment of the cells with retinoids.

EXAMPLE 12

Selective Transactivation by 9-cis-RA

The specificity for retinoids in transactivation of yeast basal promoters from site A by RXRα is illustrated in Example 11. The transactivation by either all-trans-RA or 9-cis-RA is totally unexpected because it has been recently reported that the ligand for RXRα is 9-cis-RA. In mammalian cells, all-trans-RA can be isomerized to 9-cis-RA but there is no evidence in support of a similar mechanism in yeast. To compare the effectiveness of all-trans-RA and 9-cis-RA in stimulating RXRα mediated transactivation in yeast cells, the β-gal activity produced by YEpRXRα/YRpA yeast cells in response to increasing concentrations of each of these retinoids is determined. The results in FIG. 6 show clearly that 9-cis-RA is at least 10 times more potent than all-trans-RA in stimulating β-gal activity from these cells at the same concentration of hormone ($0.1 \times 10^{-6}$M).

These results indicate that similar to mammalian cells, yeast RXRe responds selectively to 9-cis-RA and raise the possibility that yeast contain enzymes for isomerization of all-trans-RA to 9-cis-RA.

EXAMPLE 13

Screen for Antagonists or Agonists of RXRα Receptor

As shown in FIG. 7, a plate assay is validated for high throughput screening. In this assay, yeast cells containing the RXRα receptor expression plasmid and the reporter construct are inoculated in yeast media containing the chromogenic substrate, X-GAL® (a registered trademark of 5-bromo-4-chloro-3-indolyl-β-D-galactopyranoside, commercially available from Gibco BRL, Bethesda, Md.) Discs containing different hormones (all-trans-retinoic acid, 9-cis-retinoic acid, testosterone, 17-β estradiol, progesterone, thyroid hormone, cortisone and 20-hydroxyecdysone) are placed on top of the agar plate. Induction of the reporter enzyme as reflected by the formation of the blue halo is observed for 9-cis retinoic acid and all-trans-retinoic acids only.

EXAMPLE 14

Construction of Reporter Plasmid and Expression Vectors

All reporter constructs are made by cloning different double stranded oligonucleotides into a BamHI site engineered at nucleotide position −41 upstream of the apoAI gene transcription start site (+1) in a previously described construct in which the apoAI gene promoter region from −41 to +397 is fused to the bacterial chloramphenicol acetyltransferase (CAT) gene (construct −41ALCAT). Synthesis of single stranded oligonucleotides, their annealing into double stranded oligonucleotides, their ligation into the BamHI site of −41ALCAT, and their verification by DNA sequencing are as previously described in the literature. Each of these single stranded oligonucleotides is synthesized with a 5' GATC overhang to facilitate cloning into the BamHI site in −41ALCAT. The nucleotide sequence (from 5' to 3') of each of these oligonucleotides and its relative orientation in the corresponding constructs is as follows:

ACTGAACCCTTGACCCCTG (SEQ ID NO:5) (Reverse) construct A5';

CTTGACCCCTGCCCTGCAG (SEQ ID NO:6) (Reverse) construct A3';

ACTGAACTGATGACCCCTG (SEQ ID NO:7) (Forward) construct M2;

ACTGAACTTTTGACCCCTG (SEQ ID NO:8) (Reverse) construct M3;

ACTGACCCCTTGACCCCTG (SEQ ID NO:9) (Forward) construct M4;

ACTGACCTGACCCCTG (SEQ ID NO:10) (Forward) construct M5;

ACTGACCTTTTGACCCCTG (SEQ ID NO:11) (Forward) construct M6;

ACTGAACCCTTGAACCCTG (SEQ ID NO:12) (Reverse) construct M7;

ACTGAACTGAACCCTG (SEQ ID NO:13) (Forward) construct M8;

ACTGAACTGTGACCCCTG (SEQ ID NO:14) (Forward) construct M9;

ACTGACCTGTGACCCCTG (SEQ ID NO:15) (Forward) construct M10.

The vectors expressing the retinoic acid receptors RXRα, RARα, and RARβ, pMT2-RXRα, pMT2-RARα, and pMT2-RARβ respectively and the vectors expressing the hepatocyte nuclear factor 4 (HNF4), the apolipoprotein AI regulatory protein-1 (ARP-1), and the chicken ovalbumin upstream factor (Ear3-COUP-TF), pMT2-HNF4, pMT2-ARP-1 and pMT2-Ear3-COUP-TF respectively can be constructed by well-known techniques described in the literature.

EXAMPLE 15

Transient Expression Assays

Maintenance of CV-1 cells, transfection of plasmid DNA into these cells, normalization for plasmid DNA uptake by the cells and CAT and β-galactosidase (β-gal) assays are performed as previously described in the literature. The transfection mixtures contained 5 µg of each reporter plasmid, 5 µg of the β-gal expression vector pRSV-β-gal, the amounts of the pMT2-RXRα, pMT2-RARα, pMT2-RARβ, pMT2-ARP-1 and pMT2-Ear3-COUP-TF expression vectors and the appropriate amounts of the previously described control vector pMT2-UT to bring the final amount of the plasmid DNA in the transfection mixtures to a total of 17 µg. The transfection mixtures containing the expression vectors pMT2-HNF4 or pSG5-AR, 1 µg of the β-gal expression vector pCMV-β-gal instead of the vector pRSV-β-gal is used and the final amount of plasmid DNA in the transfection mixture is adjusted to a total of 13 µg as described above.

EXAMPLE 16

Transfection with Expression Vectors

For these experiments, three apoAI promoter/CAT gene fusion constructs, construct −41AI.CAT which contains the apoAI basal promoter from nucleotide −41 to nucleotide +397 fused to the CAT gene and constructs [A]−41AI.CAT and [2XA]−41AI.CAT which contain one and two copies of site A, respectively, proximal to the apoAI basal promoter in −41AI.CAT are cotransfected with various vectors expressing different members of the nuclear hormone receptor superfamily into CV-1 cells in the presence or absence of the corresponding ligands. The CAT activity in extracts from these cells is determined, normalized for DNA uptake by the cells and expressed relative to the normalized CAT activity of the construct −41AI.CAT (relative CAT activity).

EXAMPLE 17

Conferral of Responsiveness to RXRα and HNF4 by Distinct Sequences Within the apoAI Gene Site A The minimal DNA sequence requirements are determined for responsiveness of site A to RXRα in the presence of RA and to HNF4. For these experiments, two oligonucleotides spanning different portions of site A are cloned proximal to the apoAI basal promoter in the construct −41AI.CAT and the resulting constructs are tested for their responsiveness to RXRα in the presence of RA and to HNF4 in CV-1 cells. More specifically site A,5'-AC<u>TGAAC</u>CC<u>TTGACCCC</u> <u>TGCCCT</u>-3' (SEQ ID NO:16) is composed of three imperfect TGACC repeats (underlined) and one of these oligonucleotides spans the two 5' repeats, 5'-AC<u>TGAACCCT</u> <u>TGACC</u>TG-3' (SEQ ID NO:17) (oligo A5'), while the other oligonucleotide spans the two 3' repeats, 5'-CT<u>TGACCCC</u> <u>TGCCCT</u>-3' (SEQ ID NO:18) (oligo A3'). The constructs containing the oligos A5' and A3' are named [A5']−41AI.CAT and [A3']−41AI.CAT respectively. The construct [A5']−41AI.CAT, but not the construct [A3']−41AI.CAT, is efficiently transactivated by RXRα in the presence of RA, and both of these constructs are transactivated by HNF4. A similar construct containing a mutated version of site A, 5'-AC<u>TGAACCCGGGACCCCTGCCCT</u>-3' (SEQ ID NO:19) (oligo Amut), in which two T residues in site A have been substituted by G residues (bolded), does not respond to either RXRα in the presence of RA or to HNF4.

These results indicate that the central TGACC repeat in site A is important for its responsiveness to both RXRα in the presence of RA and HNF4 and that while the portion of site A containing the two 5' TGACC imperfect repeats is sufficient for responsiveness to both RXRα in the presence of RA and HNF4, the portion of site A containing the two 3' TGACC imperfect repeats is sufficient for responsiveness to HNF4 but not to RXRα in the presence of RA. These observations raise the possibility that different portions of site A play an important role in the sorting and integration of different signals transmitted by these transcriptional regulators.

EXAMPLE 18

Figure 8:
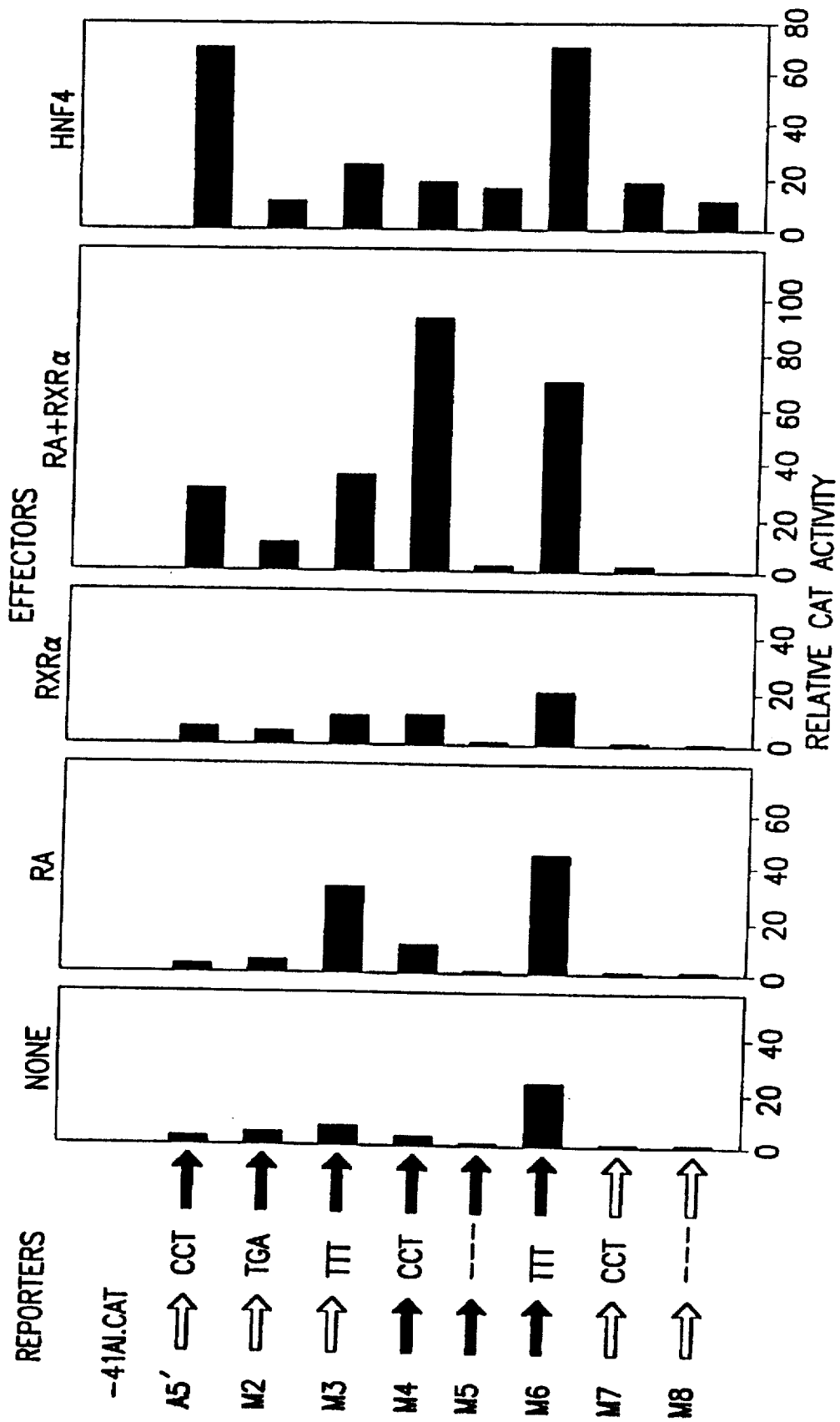
FIG. 8 illustrates that different structural determinants in site A5' confer responsiveness to RXRα and HNF4. A collection of reporters similar to the known [A]-41ALCAT but containing different novel mutated versions of site A5' (M2 through M8; open arrows: TGAAC, solid arrows: TGACC) are tested for their responsiveness to RXRα in the presence or absence of RA and to HNF4 by transient transfection assays into CV-1 cells. Each of the reporter constructs is cotransfected with 2 µg of the vectors expressing the indicated receptors in the presence or absence of the corresponding ligands at a concentration of $10^{-6}$M for RA and $10^{-7}$M for all other ligands into CV-1 cells. The CAT activity in extracts from these cells is normalized for DNA uptake by the cells by conventional methods, and expressed relative to the normalized CAT activity of the construct –41ALCAT in the absence of cotransfected receptor expression vectors or any ligands (Relative CAT Activity). The data represent the average of at least two independent experiments.

Structural Determinants in Site A5' and Structural Adaptations of HNF4 Control Transactivation of Site A5' by RXRα and HNF4 Respectively Several different members of the nuclear hormone receptor superfamily bind efficiently to site A. Although it is currently unknown whether all of these transcriptional regulators bind to the same or different portions of site A, the results in the previous example strongly suggest that RXRα and HNF4 bind to the same portion of site A, namely the site A5'. This has also been directly demonstrated by electrophoretic mobility shift assays. The flexibility of site A5' in binding of different members of the nuclear hormone receptor superfamily implies that either site A5' has evolved by incorporating the structural determinants required for binding of either RXRα or HNF4 or that RXRα and HNF4 can undergo structural adaptations to accommodate binding to site A in a manner similar to that described recently for binding of EAR3-COUP-TF to different sites. To discriminate between these possibilities several variants of site A5' containing nucleotide substitutions in one or the other TGACC repeats and/or substitutions or deletions of the sequence between these repeats (spacer) are cloned proximal to the apoAI basal promoter in −41AI.CAT. The resulting constructs are transfected into CV-1 cells alone, in the presence of RA, and together with the RXRα expression vector in the presence or absence of RA or together with the HNF4 expression vector. The CAT activity in extracts from these cells is determined, normalized and the data are used to construct the bar plots in FIG. 8. The results in FIG. 8 show that with the exception of the construct containing the site A5' variant in which the first repeat is TGACC instead of TGAAC and the spacer is TTT instead of CCT (construct M6), none of the other constructs expresses CAT activity at levels substantially greater than that expressed from the construct −41AI.CAT. In the presence of RA, only the construct containing site A5' variant in which the spacer is TTT instead of CCT (construct M3), the construct containing the site A5' variant in which the first repeat is TGACC instead of TGAAC (construct M4) and the construct M6 express CAT activity at levels substantially greater than that expressed from the construct −41AI.CAT. The CAT activity expressed by the constructs M3, M4 and M6 in the presence of RA is 4.5, 2.5 and 1.9-fold greater, respectively, than that expressed from the same constructs in the absence of RA, suggesting that all three of these constructs respond to RA receptors endogenous in CV-1 cells. In the presence of cotransfected RXRe but in the absence of RA only the constructs M3, M4 and M6 express CAT activity at levels substantially greater than that expressed from the construct −41AI.CAT, although the levels of expression are generally lower than those expressed from the same constructs in the presence of RA but in the absence of cotransfected RXRα. In the presence of cotransfected RXRα and RA, the constructs [A5']−41AI.CAT, M3, M4 and M6 express 4.8, 3, 7 and 3.1-fold greater levels of CAT activity, respectively, compared to that expressed from the same constructs cotransfected with RXRα in the absence of RA. However, for constructs M3 and M6, nearly all of this stimulation of CAT activity can be accounted for by the transactivation from the CV-1 cell endogenous RA receptors (FIG. 8, compare the relative CAT activities of constructs M3 and M6 in the presence of RA with those of the same constructs in the presence of cotransfected RXRα and RA) and thus it seems to be independent of the cotransfected RXRα. In contrast for the constructs [A5']−41AI.CAT and M4 this stimulation of CAT activity is at least 7-fold greater than that due to transactivation by the CV-1 cell endogenous RA receptors (FIG. 8 compare the relative CAT activities of construct [A5']−41AI.CAT and M4 in the presence of RA with those of the same constructs in the presence of cotransfected RXRα and RA) suggesting that it is dependent on the cotransfected RXRα. Thus it appears that a sequence of two TGACC direct repeats separated by the trinucleotide spacer CCT defines an RA responsive element that responds efficiently and selectively to RXRα over other RA receptors endogenous to CV-1 cells in the presence of RA. The nucleotide sequence in the spacer of this element appears to play an important role in both the level of responsiveness to RXRα and its ability to discriminate between CV-1 cell endogenous RA receptors and RXRα. For example, although site A5' responds preferentially to RXRα over these endogenous RAreceptors the variant site A5' in which the spacer is TTT instead of CCT (construct M3) responds efficiently to these endogenous receptors while the site A5' variant in which the spacer is TGA instead of CCT (construct M2) responds very poorly to both RXRα and these endogenous RA receptors (FIG. 8). In addition to the nucleotide sequence of the spacer, the spacing between the two repeats seem to play an important role in the level of responsiveness to both RXRα and endogenous RA receptors. Thus elimination of the spacer completely abolishes responsiveness to these receptors irrespective of whether both repeats are TGACC (construct M5) or TGAAC (construct M8). Finally, in addition to the nucleotide sequence in the spacer, and the spacing between the two TGACC direct repeats, the nucleotide sequence in these repeats seems to play a determinant role in the level of responsiveness to both RXRα and CV-1 cell endogenous RA receptors. For example, the variant site A5' in which the second repeat is TGAAC instead of TGACC (construct M7) responds poorly to both RXRα and CV-1 cell endogenous RA receptors. In remarkable contrast to the results described above, the cotransfection experiments with the HNF4 expression vector show that all of these constructs express CAT activity at levels substantially higher than the level expressed from the construct −41AI.CAT (FIG. 8).

Taken together, these observations indicate that the apoAI gene site A5' while preserving most of the structural determinants required for efficient and selective transactivation by RXRα and RA, accommodates structural adaptations required for transactivation by HNF4.

EXAMPLE 19

Sequence CCT in the Spacer Region Between the Two TGACC Direct Repeats of Site A5' Determines its Efficient Responsiveness to RXRα and RA The results in the previous example show that the nucleotide sequence CCT in the spacer region between the two TGACC direct repeats is essential for the ability of RA-responsive elements containing these sequences to respond efficiently and selectively to RXRα and RA. This contrasts recently reported experimental findings indicating that a RA-responsive element in the CRBPII gene which contains the nucleotide sequence TG in the spacer region between the two TGACC direct repeats also responds efficiently and selectively to RXRα and RA. To address this issue directly, two constructs containing variants of site A5' proximal to the apoAI basal promoter in −41AI.CAT are prepared. One of these constructs contains a site A5' variant in which the spacer is TG instead of CCT (construct M9) and the other contains a site A5' variant in which the first repeat is TGACC instead of TGAAC and the spacer is TG instead of CCT (construct M10). These constructs and for the purpose of comparisons, the constructs −41AI.CAT, [A5']−41AI.CAT and M4 are transfected into CV-1 cells alone, in the presence of RA and in the presence of cotransfected RXRα in the absence or presence of RA. The CAT activity in extracts from these cells is determined and normalized. The CAT activity expressed by the constructs M9 and M10 in the presence of RXRα and RA is less than 3-fold greater than that expressed by the same construct in the presence of cotransfected RXRα but in the absence of RA. Similar results are also obtained with the construct M2 which contains a site A5' variant in which the spacer is TGA instead of CCT (see FIG. 8). In striking contrast, and consistent with the data in FIG. 8, the CAT activity expressed by the constructs [A5']–41ALCAT and M4 in the presence of cotransfected RXRα and RA is at least 5-fold greater than that expressed by the same constructs in the presence of cotransfected RXRα but in the absence of RA. It therefore appears that although the nucleotide sequences TG or TGA in the spacer region between the two TGACC direct repeats does not interfere with the ability of RA responsive elements to respond selectively to RXRα over other RA receptors endogenous to CV-1 cells, the magnitude of this responsiveness is drastically diminished compared to that of RA responsive elements containing the nucleotide sequence CCT in the spacer region between these two repeats.

It is therefore concluded that the ability of site A5' to respond efficiently to RXRα and RA is greatly dependent upon the presence of the nucleotide sequence CCT in the spacer region between the two TGACC direct repeats in site A5'.

EXAMPLE 20

Sequence CCT in the Spacer Region Between the Two TGACC Direct Repeats of Site A5' Determines its Selective Responsiveness to RXRα and RA As shown above, the remarkable capacity of site A5' and the variant of site A5' in the construct M4 to discriminate between RXRα and other RA receptors endogenous to CV-1 cells is drastically diminished when the sequence CCT in the spacer region between the two TGACC direct repeats of these sites is replaced by the sequence TTT. Thus when the spacer is CCT, these sites respond efficiently to RXRα and very inefficiently to CV-1 cell endogenous RA receptors in the presence of RA. However, when the spacer is TTT instead of CCT these sites respond efficiently to these endogenous RA receptors and very inefficiently to RXRα in the presence of RA (FIG. 8, compare construct [A5']–41ALCAT with M3 and construct M4 with M6). Thus it appears that the sequence CCT in the spacer, in addition to its importance for efficient responsiveness of site A5' to RXRα and RA (see previous example), plays a fundamental role in the ability of this site to respond selectively to RXRα over other RA receptors endogenous to CV-1 cells in the presence of RA. To show this directly, it is determined whether the construct M3, which contains a site A5' variant with the spacer TTT instead of CCT, responds to RXRα and RA. This construct is already seen to be activated by RA receptors endogenous to CV-1 cells in the presence of RA. And it is known that ARP-1 binding to hormone response elements eliminates endogenous basal responsiveness and that subsequent cotransfection with exogenous transactivators establishes transactivator dependent transcriptional activation. Specifically, a construct similar to M3, but containing two copies of the same oligonucleotide used to generate M3 (construct 2XM3) is cotransfected with increasing amounts (10, 20, 50, 100 and 200 ng) of the ARP-1 expression vector, or a constant amount (50 ng) of the ARP-1 expression vector and increasing amounts (50 and 500 ng) of the RXRα expression vector or, as a control, a constant amount (50 ng) of the ARP-1 expression vector and increasing amounts (50 and 500 ng) of the RARα expression vector. The CAT activity in extracts from these cells is determined, normalized, and used to construct the bar plots in FIG. 9. The results in FIG. 9 show that the high levels of CAT activity expressed from the construct 2XM3 in CV-1 cells in the presence of RA is completely eliminated by increasing amounts of cotransfected ARP-1. Moreover, the results show that the presence of only 50 ng of the ARP-1 expression vector in the cotransfection mixtures inhibits CAT expression by over 80% and that inclusion of 50 ng or 500 ng of the RXRα expression in these mixtures does not reverse this inhibition. In striking contrast, inclusion of only 50 ng of the RARα expression vector in these mixtures completely reverses the ARP-1 mediated inhibition (FIG. 9). Inclusion of 500 ng of the RARα expression vector in these mixtures reverses the ARP-1 mediated inhibition and further stimulates CAT expression by more than 2-fold over that expressed from the construct 2XM3 in the absence of cotransfected ARP-1 but in the presence of RA (FIG. 9).

These results indicate that the sequence CCT in the spacer region between the two TGACC direct repeats in site A5' plays a determinant role in the capacity of this site to respond selectively to RXRα over other RA receptors endogenous to CV-1 cells in the presence of RA. Furthermore, these results suggest that the sequence TTT in the spacer region between the two TGACC repeats in RA responsive elements may determine their capacity to respond selectively to RA receptors other than RXRα.

In the foregoing, there has been provided a detailed description of particular embodiments of the present invention for the purpose of illustration and not limitation. It is to be understood that all other modifications, ramifications and equivalents obvious to those having skill in the art based on this disclosure are intended to be included within the scope of the invention as claimed.

Bibliography

Apostolopoulos, J. J., La Scala, M. J. and Howlett, G. J. (1988). The effect of triiodothyronine on rat apolipoprotein A-I and A-IV gene transcription. Biochem. Biophys. Res. Com. 154:997–1002.

Bagchi, M. K., Elliston, J. F., Tsai, S., Y., Edwards, D. P., Tsai, M-J. and O'Malley, B. W. (1988). Steroid hormone-dependent interaction of human progesterone receptor with its target enhancer element. Mol. Endocrinol. 2:1221–1229.

Beato, M. (1989). Gene regulation by steroid hormones. Cell 56:335–344.

Bradford, M. M. (1976). A rapid and sensitive method for quantitation of microgram quantities of protein utilizing principle of protein-dye binding. Anal. Biochem. 72:248–254.

Bugge, T. H., Pohl, J., Lonnoy, O. and Stunnenberg, H. G. (1992). RXRα, a promiscuous partner of retinoic acid and thyroid hormone receptors. EMBO J. 11:1409–1418.

Callard, G. V. and Mak, P. (1985). Exclusive nuclear location of estrogen receptors in Squalus testis. Proc. Natl. Aca. Sci (U.S.A.). 82:1336–1340.

Carson, M. A., Tsai, M-J., Conneely, O. M., Maxwell, B. L., Clark, J. H. Dobson, A. D. W., Elbrecht, A., Toft, D. O., Schrader, W. T. and O'Malley, B. W. (1987). Structure-function properties of the chicken progesterone receptor A synthesized from complementary deoxyribonucleic acid. Mol. Endocrinol. 11:791–801.

Chang, D., Kokontis, J. and Liao, S. (1988). Molecular cloning of human and rat complementary DNA encoding androgen receptors. Science 240: 324–326.

Courey, A., Holtzman, D. A., Jackson, S. P. and Tjian, R. (1989). Synergistic activation by the glutamine-rich domains of human transcription factor sp1. Cell 59:827–836.

de The, H., Vivanco-Ruiz, M. M., Tiollais, P., Stunnenberg, H. and Dejean, A. (1990). Identification of a retinoic acid responsive element in the retinoic acid receptor β gene. Nature (London) 343:177–180.

Dobson, A. D. W., Conneely, O. M. Beattie, W., Maxwell, B. L., Mak P., Tsai, M-J., Schrader, W. T. and O'Malley, B. W. (1989). Mutational analysis of chicken progesterone receptor. J. Biol. Chem. 264:4207–4211.

Durand, B., Saunders, M., Leroy, P., Leid, M. and Chambon, P. (1992). All-trans and 9-cis-retinoic acid induction of CRABPII transcription is mediated by RAR-RXR heterodimers bond to DR1 and DR2 repeated motifs. Cell 71:73–85.

Evans, R. M. (1988). The steroid and thyroid hormone receptor superfamily. Science 240:889–895.

Godowski, P. J., Picard, D. and Yamamoto, K. R. (1988). Signal transduction and transcriptional regulation by glucocorticoid receptor-lexA fusion proteins. Science 241:812–816.

Groyer, A., Schweizer-Groyer, G., Cadepond, F., Mariller, M. and Baulieu, E. E. (1987). Anti-glucocorticosteroid effects suggest why steroid hormone is required for receptors to bind DNA in vivo but not in vitro. Nature 328:624–628.

Hermann, T., Hoffmann, B., Zhang, X.-K., Tran, P., and Pfahl, M. (1992). Heterodimeric receptor complexes determine 3,5,3'-triiodothyronine and retinoid signaling specificities. Mol. Endo. 6:1153–1162.

Heyman, R. A., Mangelsdorf, D. J., Dyck, J. A., Stein, R. B., Eichele, G., Evans, R. M., and Thaller, C. (1992). 9-Cis-retinoic acid is a high affinity ligand for the retinoid X receptor. Cell 68:397–406.

Hope, I. and Struhl, K. (1986). Functional dissection of a eukaryotic transcriptional activator protein, GCN4 of yeast. Cell 46:885.

Karathanasis, S. K. (1992). Apolipoprotein AI gene regulation by members of the steroid/thyroid hormone receptor superfamily of ligand dependent transcription factors. In High Density Lipo-proteins and Atherosclerosis III; Miller, N. E. and Tall, A. (Eds.) Elsevier. pp. 21–32.

Klein-Hitpass, L., Schorpp, M., Wagner, U. and Ryffel, G. U. (1986). An estrogen-responsive element de-cells. Cell 46:1053–1061.

Kliewer, S. A., Umesono, K., Mangelsdorf, D. J. and Evans, R. M. (1992) Retinoid X receptor interacts with nuclear receptors in retinoic acid, thyroid hormone and vitamin $D_3$ signalling. Nature (London) 355:446–449.

Leroy, P., Nakshatri, H. and Chambron, P. (1991). Mouse retinoic acid receptor α2 isoform is transcribed from a promoter that contains a retinoic acid response element. Proc. Natl. Acad. Sci. U.S.A. 88:10138–10142.

Levin, A. A., Sturzenbecker, L. J., Kazmer, S., Bosakowski, T., Huselton, C., Allenby, G., Speck, J., Kratzeisen, C. L., Rosenberger, M., Lovey, A., and Grippo, J. F. (1992). 9-Cis-retinoic acid stereoisomer binds and activates the nuclear receptor RXRα. Nature 355:359–361.

MacGregor, G. R. and Caskey, C. T. (1989). Construction of plasmids that express E. coli β-galactosidase in mammalian cells. Nucleic Acids Res. 17:2365.

Mak, P., McDonnell, D. P., Weigel, N. L., Schrader, W. T. and O'Malley, W. B. (1989). Expression of functional chicken oviduct progesterone receptors in yeast (Saccharomyces cerevisiae). J. Biol. Chem. 264:21613–21618.

Mangelsdorf, D. J., Ong, E. S., Dyck, J. A., and Evans, R. M. (1990). Nuclear receptor that identifies a novel retinoic acid response pathway. Nature 345:224–229.

McDonnell, D. P., Pike, J. W., Drutz, D. J., Butt, T. R. and O'Malley, B. W. (1989). Reconstitution of vitamin D-responsive osteocalcin transcription unit in Saccharomyces cerevisiae. Mol. Cell. Biol. 9:3517–3523.

Miller, J. H. (1972). Experiment 48: Assay of β-galactosidase. Experiments in Molecular Genetics (Miller, J. H., ed) pp. 352–355, Cold Spring Harbor Laboratory, Cold Spring Harbor, N.Y.

Moehle, C. M., Ayanardi, M. W., Kolodny, M. R., Park, F. J. and Jones, E. W. (1986). Protease B of Saccharomyces cerevisiae: isolation and regulation of PRB1 structural gene. Genetics 115:255–265.

O'Malley, B. W. (1990). The steroid receptor superfamily: more excitement predicted for future. Mol. Endocrinol. 4:363–369.

Peterson, M. G., Tanese, N., Pugh, B. F. and Tjian, R. (1990). Functional domains and upstream activation properties of cloned human TATA binding protein. Science 248:1625–1630.

Picard, D., Khursheed, B., Garabedian M. J., Fortin, M. G., Lindquist, S. and Yamamoto, K. R. (1990). Reduced levels of hsp90 compromise steroid receptor action in vivo. Nature 348: 166–169.

Privalsky, M. L., Sharif, M. and Yamamoto, K. R. (1990). The viral erbA oncogene protein, a constitutive repressor in animal cells, is a hormone-regulated activator in yeast. Cell 63: 1277–1286.

Rottman, J. N., Widom, R. L., Nadal-Ginard, B., Mahdavi, V., and Karathanasis, S. K. (1991). A retinoic acid response element in the apolipoprotein AI gene distinguishes between two different retinoic acid response pathways. Mol. Cell Biol. 11:3814–3820.

Sastry, K. N., Seedorf, U. and Karathanasis, S. K. (1988). Different cis-acting elements control expression of the human apolipoprotein AI gene in different cell types. Mol. Cell Biol. 8: 605–614.

Sorci-Thomas, M. and Kearns, M. W. (1991). Transcriptional regulation of the apolipoprotein A-I gene. Species-specific expression correlates with rates of gene transcription. J. Biol. Chem. 266:18045–18050.

Tora, L., Gronemeyer, H., Turcotte, B., Gaub, M. P. and Chambon, P. (1988). The N-terminal region of chicken progesterone receptor specifies target gene activation. Nature 33:185–188.

Trapman, J., Klaassen, P., Kuiper G. G. J. M., van der Korput, J. A. G. M., Faber, P. W., van Rooij, J. C. J., Geurts van Kessel, A., Voorhorst, M. M., Mulder, E. and Brinkmann, A. O. (1988). Cloning, structure and expression of a cDNA encoding the human androgen receptor. Biochem. Biphys. Res. Commun. 153:241–248.

Walsh, A., Ito, Y. and Breslow, J. L. (1989). High levels of human apolipoprotein AI in transgenic mice result in increased plasma levels of small high density lipoprotein (HDL) particles comparable to human HDL. J. Biol. Chem. 264:6488–6494.

Widom, R. L., Ladias, J. A. A., Kouidou, S. and Karathanasis, S. K. (1991). Synergistic interactions between transcription factors control expression of the apolipoprotein AI gene in liver cells. Mol. Cell Biol. 11:677–687.

Widom, R. L., Rhee, M. and Karathanasis, S. K. (1992). Repression by ARP-1 sensitizes apolipo-protein AI gene responsiveness to RXRα and retinoic acid. Mol. Cell Biol. 12:3380–3389.

Yamamoto, K. R. (1985). Steroid receptor regulated transcription of specific genes and gene networks. Annu. Rev. Genet. 19:209–252.

Zhang, X-K., Hoffmann, B. B-V, P., Graupner, G. and Pfahl, M. (1992). Retinoid X receptor is an auxiliary protein for thyroid hormone and retinoic acid receptors. Nature (London) 355:441-446.

Zhang, X-K, Lehmann, J., Hoffmann, B., Dawson, M. I., Cameron, J., Graupner, G., Hermann, T., Tran, P., and Pfahl, M. (1992). 9-cis-retinoic acid induces RXR homodimer formation: A mechanism defining a novel retinoid pathway. Nature (London) 358:587-591.

What is claimed is:

1. A prokaryotic or eukaryotic host cell stably transformed or transfected by an expression vector containing a cDNA sequence encoding a retinoid X receptor and a reporter plasmid containing an apolipoprotein AI gene site A mutant comprising a nucleotide sequence selected from the group consisting of SEQ ID NOS: 7–15 and 17.

2. The host cell according to claim 1, which comprises a yeast strain carrying an expression vector identified as BJ YEpRXRα, having the ATCC designation number 74197.

3. The host cell according to claim 1, which comprises a yeast strain carrying an expression vector and a reporter plasmid identified as BJ YEpRXRα/YRpA, having the ATCC designation number 74196.

4. The host cell according to claim 1, which comprises a yeast strain carrying a reporter plasmid identified as BJ YRpA, having the ATCC designation number 74195.

5. The host cell according to claim 1, which comprises a DH5α strain of E. coli carrying an expression vector identified as YEpRXRα, having the ATCC designation number 69145.

6. The host cell according to claim 1, which comprises a DH5α strain of E. coli carrying a reporter plasmid identified as YRpA, having the ATCC designation number 69144.

7. An HB101 strain of E. coli carrying the reporter plasmid identified as [M6]–41ALCAT, having the ATCC designation number 69169.

8. An HB101 strain of E. coli carrying the reporter plasmid identified as [M4]–41ALCAT, having the ATCC designation number 69170.

9. An HB101 strain of E. coli carrying the reporter plasmid identified as [M3]–41ALCAT, having the ATCC designation number 69168.

10. A gene sequence comprising a nucleotide sequence comprising two TGACC imperfect direct repeats separated by the trinucleotide spacer CCT having the nucleotide sequence of SEQ ID NO: 10, wherein the protein expressed by said gene sequence responds selectively to a retinoid x receptor.

11. A gene sequence comprising a nucleotide sequence comprising two TGACC imperfect direct repeats separated by the trinucleotide spacer TTT having the nucleotide sequence of SEQ ID NO: 8 or SEQ ID NO: 9, wherein the protein expressed by said gene sequence responds to a receptor other than a retinoid X receptor.

* * * * *

UNITED STATES PATENT AND TRADEMARK OFFICE
CERTIFICATE OF CORRECTION

PATENT NO. : 5,700,682

DATED : December 23, 1997

INVENTOR(S) : Paul Mak and Sotirios K. Karathanasis

It is certified that error appears in the above-indentified patent and that said Letters Patent is hereby corrected as shown below:

Col. 10, line 3: change "$5x10^-5M$" to --$5x10^{-5}M$--.
Col. 14, line 27: change "RXRe" to --RXR$\alpha$--.
Col. 17, line 36: change "RXRe" to --RXR$\alpha$--.

Signed and Sealed this

Fifth Day of October, 1999

Q. TODD DICKINSON

*Attest:*

*Attesting Officer*    Acting Commissioner of Patents and Trademarks

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TACGGCCGAT GGACACCAAA CATTTCCTG     29

( 2 ) INFORMATION FOR SEQ ID NO:2:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

TAGTCGACTC CACCTCATTC TCGTTCCG     28

( 2 ) INFORMATION FOR SEQ ID NO:3:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

ATGTCGACCA GCAGCGCCAA CGAGGAC     27

( 2 ) INFORMATION FOR SEQ ID NO:4:

( i ) SEQUENCE CHARACTERISTICS:
        ( A ) LENGTH: 35 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

TACACACAGT GCTAACTCAT TTGGTGCGGC GCCTC     35

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: double (D) TOPOLOGY: linear (ii) MOLECULE TYPE: DNA (genomic)

(xi) SEQUENCE DESCRIPTION: SEQ ID NO:5:

ACTGAACCCT TGACCCCTG                                          19

(2) INFORMATION FOR SEQ ID NO:6:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:6:

CTTGACCCCT GCCCTGCAG                                          19

(2) INFORMATION FOR SEQ ID NO:7:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

ACTGAACTGA TGACCCCTG                                          19

(2) INFORMATION FOR SEQ ID NO:8:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

ACTGAACTTT TGACCCCTG                                          19

(2) INFORMATION FOR SEQ ID NO:9:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

ACTGACCCCT TGACCCCTG                                          19

(2) INFORMATION FOR SEQ ID NO:10:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

ACTGACCTGA CCCCTG                                                              16

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

ACTGACCTTT TGACCCCTG                                                           19

(2) INFORMATION FOR SEQ ID NO:12:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:12:

ACTGAACCCT TGAACCCTG                                                           19

(2) INFORMATION FOR SEQ ID NO:13:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:13:

ACTGAACTGA ACCCTG                                                              16

(2) INFORMATION FOR SEQ ID NO:14:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:14:

ACTGAACTGT GACCCCTG                                                            18

(2) INFORMATION FOR SEQ ID NO:15:

(i) SEQUENCE CHARACTERISTICS:
        (A) LENGTH: 18 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:15:

ACTGACCTGT GACCCCTG                                                            18

(2) INFORMATION FOR SEQ ID NO:16:

( i ) SEQUENCE CHARACTERISTICS:
    ( A ) LENGTH: 23 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:16:

ACTGAACCCT TGACCCCTGC CCT　　　　　　　　　　　　　　　　　　23

( 2 ) INFORMATION FOR SEQ ID NO:17:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:17:

ACTGAACCCT TGACCTG　　　　　　　　　　　　　　　　　　　　17

( 2 ) INFORMATION FOR SEQ ID NO:18:

( i ) SEQUENCE CHARACTERISTICS:
        ( A ) LENGTH: 15 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:18:

CTTGACCCCT GCCCT　　　　　　　　　　　　　　　　　　　　　15

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:19:

ACTGAACCCG GGACCCCTGC CCT　　　　　　　　　　　　　　　　　23